(12) United States Patent
Nahum

(10) Patent No.: US 10,076,279 B2
(45) Date of Patent: Sep. 18, 2018

(54) SYSTEM AND METHOD FOR A COMPACT EEG HEADSET

(71) Applicant: Neba Health, LLC, Augusta, GA (US)

(72) Inventor: Altan Nahum, Boulder, CO (US)

(73) Assignee: Neba Health, LLC, Augusta, GA (US)

( * ) Notice: Subject to any disclaimer, the term of this patent is extended or adjusted under 35 U.S.C. 154(b) by 574 days.

(21) Appl. No.: 14/521,360

(22) Filed: Oct. 22, 2014

(65) Prior Publication Data

US 2015/0112153 A1 Apr. 23, 2015

Related U.S. Application Data

(60) Provisional application No. 61/894,362, filed on Oct. 22, 2013, provisional application No. 61/906,799, filed on Nov. 20, 2013.

(51) Int. Cl.
*A61B 5/0478* (2006.01)
*A61B 5/00* (2006.01)
*A61B 5/11* (2006.01)

(52) U.S. Cl.
CPC .......... *A61B 5/6803* (2013.01); *A61B 5/0478* (2013.01); *A61B 5/11* (2013.01); *A61B 5/6814* (2013.01)

(58) Field of Classification Search
CPC ... A61B 5/04; A61B 5/04002; A61B 5/04004; A61B 5/0404; A61B 5/0408; A61B 5/04085; A61B 5/04087; A61B 5/0416; A61B 5/0476; A61B 5/0478;
(Continued)

(56) References Cited

U.S. PATENT DOCUMENTS 3,659,614 A * 5/1972 Jankelson .............. A61N 1/321
607/139
4,678,865 A 7/1987 Sherwin
(Continued)

FOREIGN PATENT DOCUMENTS

CA 2675507 7/2008
EP 1238629 12/2005
(Continued)

OTHER PUBLICATIONS

Agence France-Presse (Sep. 16, 2011) "Hitachi unveils headset to study brain activity," *Agence France-Presse*. http://www.timesofmalta.com/articles/view/20110916/world/Hitachi-unveils-headset-to-study-brain-activity.384941 [Last Accessed Nov. 14, 2014].
(Continued)

*Primary Examiner* — Eunhwa Kim
(74) *Attorney, Agent, or Firm* — Macheledt Bales LLP; Jennifer L. Bales

(57) ABSTRACT

An EEG headset including an amplifier assembly, a headband assembly formed of a right and a left headband arm and an amplifier platform, a right and left lateral support assembly, at least one hinge assembly connecting at least one of the right or left lateral support assemblies to at least one of the right or left curved arms, and at least one EEG electrode assembly formed of a lead and an electrode. The electrode is in electrical communication with the amplifier assembly via electrical connections within the headset assembly and one of the right and left lateral support assembly.

28 Claims, 30 Drawing Sheets

(58) Field of Classification Search
CPC .. A61B 5/0482; A61B 5/0484; A61N 1/0526; A61N 1/0529; A61N 1/0531; A61N 1/0534
See application file for complete search history.

(56) References Cited

U.S. PATENT DOCUMENTS

| | | | |
|---|---|---|---|
| 4,890,630 A * | 1/1990 | Kroll | A61B 5/04085 128/902 |
| 5,273,037 A | 12/1993 | Itil et al. | |
| 6,154,669 A * | 11/2000 | Hunter | A61B 5/0478 600/383 |
| 6,301,493 B1 | 10/2001 | Marro et al. | |
| 6,381,481 B1 | 4/2002 | Lavendowski et al. | |
| 6,510,340 B1 | 1/2003 | Jordan | |
| 6,654,966 B2 | 12/2003 | Rolla | |
| D565,735 S | 4/2008 | Washbon | |
| 7,551,952 B2 | 6/2009 | Gevins et al. | |
| 8,271,075 B2 | 9/2012 | Chuang et al. | |
| 8,364,255 B2 | 1/2013 | Isenhart et al. | |
| 8,389,862 B2 | 3/2013 | Arora et al. | |
| 8,428,681 B2 | 4/2013 | Wilson et al. | |
| 2005/0197556 A1 | 9/2005 | Stoler | |
| 2007/0225585 A1* | 9/2007 | Washbon | A61B 5/0478 600/393 |
| 2010/0239114 A1 | 9/2010 | Wada | |
| 2011/0004089 A1 | 1/2011 | Chou | |
| 2011/0015503 A1 | 1/2011 | Joffe et al. | |
| 2011/0129111 A1* | 6/2011 | Santiago | H04R 5/0335 381/379 |
| 2011/0270117 A1* | 11/2011 | Warwick | A61B 5/0476 600/544 |
| 2012/0123290 A1 | 5/2012 | Kidmose et al. | |
| 2012/0143020 A1 | 6/2012 | Bordoley et al. | |
| 2012/0190959 A1* | 7/2012 | Hayakawa | A61B 5/0478 600/383 |
| 2012/0209101 A1 | 8/2012 | Kidmose et al. | |
| 2012/0226127 A1 | 9/2012 | Asjes et al. | |
| 2012/0295589 A1 | 11/2012 | Alexander et al. | |
| 2012/0296390 A1* | 11/2012 | Nakashima | A61B 5/0476 607/45 |
| 2012/0330125 A1 | 12/2012 | Wilson et al. | |
| 2013/0039509 A1 | 2/2013 | Chuang et al. | |
| 2013/0079659 A1 | 3/2013 | Akhadov et al. | |
| 2013/0085363 A1 | 4/2013 | Wada et al. | |
| 2013/0172721 A1 | 7/2013 | McPeck et al. | |
| 2013/0231545 A1 | 9/2013 | Wilson et al. | |
| 2013/0274583 A1* | 10/2013 | Heck | A61B 5/0488 600/383 |
| 2014/0213874 A1* | 7/2014 | Tong | A61B 5/0478 600/383 |

FOREIGN PATENT DOCUMENTS

| | | |
|---|---|---|
| EP | 2260760 | 12/2010 |
| EP | 2474263 | 5/2013 |
| WO | WO 1999/034865 | 7/1999 |
| WO | WO 2001/013791 | 3/2001 |
| WO | WO 2003/005897 | 1/2003 |
| WO | WO 2004/034870 | 4/2004 |
| WO | WO 2004/112604 | 12/2004 |
| WO | WO 2005/094674 | 10/2005 |
| WO | WO 2008/109699 | 9/2008 |
| WO | WO 2009/102430 | 8/2009 |

OTHER PUBLICATIONS

Degans (Apr. 10, 2012) "Imec, Holst Centre and Panasonic Present Wireless Low-power Active-Electrode EEG Headset," *Imec News.* http://www2.imec.be/be_en/press/imec-news/imeceeg2012.html [Last Accessed Nov. 14, 2014].

Emotiv (2014—Month Unknown) "Emotiv Insight Product Sheet 2014," http://emotiv.com/product-specs/Emotiv%20Insight%20Product%20Sheet%202014.pdf [Last Accessed Nov. 14, 2014].

Shindou (Apr. 8, 2010) "Hitachi to Launch Wearable Brain Analyzer," *Nikkei Technology Online.* http://techon.nikkeibp.co.jp/english/NEWS_EN/20100408/181731/ [Last Accessed Nov. 14, 2014].

Thai (Dec. 29, 2012) "WiiThink by Jonathan Thai," *Coroflot.* http://www.coroflot.com/jthai21/WiiThink [Last Accessed Nov. 14, 2014].

Uncle Milton Industries (2009) "Star Wars Force Trainer," *Uncle Milton Industries, Inc.* http://unclemilton.com/manuals/force_trainer.pdf [Last Accessed Nov. 14, 2014].

Van-Bavel et al. (2008) "Wearable Battery-free Wireless 2-Channel EEG Systems Powered by Energy Scavengers," *Sensors and Transducers Journal.* 94(7):103-115. http://www.sensorsportal.com/HTML/DIGEST/july_08/P_300.pdf [Last Accessed Nov. 14, 2014].

Wolfson (Aug. 1, 2014) "Muse Headband Can Read Your Brainwaves Using EEG," *Newsweek.* http://www.newsweek.com/muse-headband-can-read-your-brainwaves-using-eeg-262502 [Last Accessed Nov. 14, 2014].

* cited by examiner

2600

aligning the sagittal plane measurement start marker located at the proximal end of a measurement strip with the user's nasion
2602 locating where the user's inion meets a measurement scale at the distal end of the measurement strip
2604 reading a measurement from the measurement scale corresponding to where the inion meets the measurement scale
2606 identifying on a locator scale at the proximal end of a headset locator a locator measurement corresponding to the read measurement
2608 aligning the locator measurement with the user's nasion
2610 identifying a center point of the user's head at the distal end of the headset locator for accurately fitting the EEG headset to the user's head
2612

FIG. 26

SYSTEM AND METHOD FOR A COMPACT EEG HEADSET

CROSS-REFERENCE TO RELATED APPLICATIONS

This application claims the benefit of priority of U.S. Provisional Application Nos. 61/894,362 filed Oct. 22, 2013, and 61/906,799 filed Nov. 20, 2013. Both of the aforementioned applications are incorporated herein by reference in their entireties.

SUMMARY OF THE INVENTION

Electroencephalography (EEG) is a measure of the time varying electrical potentials of the brain as distributed over extracranial skin surfaces. EEG systems amplify, record, process, and display brain electrical potentials and, often in support of this, auricular (ear), ocular (eye), and muscle electrical potentials. The EEG interface to the subject typically consists of multiple discrete electrodes that assist in converting differential surface potentials into a signal of electrical form. These electrical signals are then transferred by electrical conduction to an electronic system for amplifying, recording, and processing. The raw or processed output can further be used for analysis, display, reporting, self-monitoring, and control of mechanisms, software, and devices. In medical diagnostic and assessment applications, for instance, a medical practitioner is able to make clinical decisions based on the EEG system outputs.

Though subdermal and subdural electrodes are sometimes employed, most EEG systems use surface electrodes that interface with a conductive medium to improve electrical conduction at the electrode-skin interface. Typically, the conductive medium is in the form of a paste, gel, or solution. In some instances, the conductive medium maintains a mechanical bond to the skin. In addition or in other instances, a mechanical bond is facilitated by an apparatus or material that exerts pressure on the electrode towards the skin. Pressuring the electrode against the skin may also be used in the absence of a conductive medium, as in the case of dry contact and non-contact (e.g. capacitive) electrodes. In systems that pressure electrodes against the skin, the pressure mechanisms can take the form of, for instance, elastic fabrics or membranes, elastomeric cylinders or nets, embracing or enveloping bands, flexible or semi-rigid arms, partially or wholly circumferential bands or straps, screws, pistons, or helical springs. In the case of auricular electrodes, clamp springs are sometimes used to maintain contact pressure against the ear lobes.

Some EEG systems, including traditional ones, do not use a head-worn, electrode-bearing apparatus and do not exert pressure against electrodes towards the scalp. Instead, a conductive medium with adhesive properties is applied to a disc or cup electrode to help maintain adhesion to the skin. The electrode is permanently or temporarily attached to an insulated lead wire for connection to an EEG acquisition unit. Electrodes in this type of system can be accurately placed at desired locations. However, placement is complicated by the need for numerous measurements, calculations, and markings and thus this method is time consuming and prone to multiple sources of error. In most instances, adhesive pastes are applied by the user to individual electrodes, and this contributes to overall inefficiency. Pastes also contaminate the hands, gloved or not, wherein they may be deposited at unintended sites. Adhesion to areas with dense hair is in general problematic and in some instances requires use of tape, bandages, or paste-filled gauze. The attached leads in this type of system can contribute significantly to noise due to motion/triboelectric effects and can be susceptible to entanglement. Further, as subject anxiety is of practical concern, the multiple leads emanating from the scalp can be unnerving and eerie to subjects. This visible lead configuration also causes potential users to perceive the system as complex, unwieldy, and unprofessional.

Some of the pitfalls of discrete electrode EEG systems are overcome by systems using elastic caps, tubes, or nets that exert pressure over the scalp. These systems apply pressure directly or indirectly: either on electrodes themselves or on additional pressure or suspension mechanisms that contain electrodes. This optionally permits use of electrodes that do not require adhesive pastes for attachment. There is typically some time savings in these elastic systems in the attachment phase relative to fully discrete electrode systems since electrodes can be pre-assembled at designated locations on the elastic elements.

However, there are also disadvantages of elastic systems. While electrode placement is automated and less cumbersome, placement accuracy and reliability may suffer due to elastic non-uniformity of the elastic elements when stretched over the head. This non-uniformity can stem from variation in head shape and hair morphology that contributes to localized frictional and tensional deviations of the elastic elements. Pressure-related discomfort is a further disadvantage of these systems, as is the fact that even high elastic ratio elastic elements do not adequately or comfortably cover a wide range of head sizes (e.g., spanning a head size range of small children to adults). To accommodate this size range, manufacturers must support and users must select from a plurality of system sizes (or alternatively, the system must allow for fit adjustment, which may lead to electrode misalignment and require compensatory electrode adjustment). Additionally, insufficient elastic force against the top of the head in many of these systems often necessitates use of a chin or chest strap, which increases overall discomfort and contributes to motion artifact due to jaw or torso movement. In terms of maintenance, these systems use fabrics, porous materials, or morphologically difficult to clean surfaces (or component junctions) that entrap paste, gel, dirt, and other contaminates. In non-disposable versions, this contributes to cleaning inefficiency and complexity and risk of cross contamination. Disposable versions of the elastic systems can be wasteful as well as expensive on a per use basis. Some elastic-based systems are able to conceal lead wires, but all, despite their ubiquity, introduce undesirable aesthetic and affect-related attributes, including a non-professional or non-medical appearance and a sense of discomfort and/or constraint.

Another method of pressurizing electrodes against the scalp is through the use of semi-rigid arms or enveloping or embracing arms or bands. Like elastic mechanisms, semi-rigid arm/band mechanisms apply pressure directly or indirectly toward the scalp—by pressing on electrodes themselves and/or by employing additional pressure or suspension mechanisms that contain electrodes, relying on this pressure to forgo adhesive electrode pastes. Relative to fully discrete electrode systems, there is typically a time efficiency advantage in attaching these semi-rigid systems since electrodes are typically pre-assembled at designated locations on the semi-rigid element or elements. Additionally, these semi-rigid systems can be made easier to clean than fabric or porous membrane elastic systems.

However, there are a number of problems associated with these semi-rigid systems. While electrode placement is often pre-configured for efficiency, placement can be less accurate than required due to head size and shape variation. Many medical and research uses, for example, require more accurate placement than is achievable with these systems. Electrode placement inaccuracy in semi-rigid systems is not sufficiently mitigated by the inherent flexibility of the arms or bands, and means of electrode placement adjustment in the prior art do not adequately address the problem, in part due to insufficient adjustment freedom. Furthermore, adding more adjustment mechanisms (for instance, a combination of rotational and linear) can add undesirable practical complexity, both in use and in manufacturing.

Another problem associated with these semi-rigid systems is that consistent pressure is not maintained across a large range of head sizes. Pressure disparity stems in part from the elastic region stress-strain characteristics of the semi-rigid materials used in these systems. Certain portions of these semi-rigid systems are designed to maintain the system in place on the wearer. In some cases, embracing arms or bands are used to help maintain multiple areas of pressure on the head. In the systems incorporating embracing bands, conformance to differing head size and shape is further compromised because the pressure elements cover too large or too variable a surface region of the head (despite additional means of compensatory adjustment). In non-embracing (non-encircling) systems, two anatomical regions may be pressurized using clamping force, either bilaterally or on the anterior-posterior surfaces of the head. These clamping regions are typically reduced in area in order to minimize head shape and size incompatibility. However, the rigid or semi-rigid pressure interface elements of these prior art examples are either not head-conforming (thus requiring significant cushioning in an attempt to increase comfort and stability) or are located on suboptimal head regions. Such suboptimal head regions are those that are typically associated with high variance across individuals (for example, auricular or circumaural regions) and/or prone to muscle motion during ordinary head movement, vocalization, or facial expression (for example, regions inclusive of the inion, posteroinferior skull, forehead, or subaural musculature).

In terms of practical and anxiety-reducing design, lead wires are concealed in some semi-rigid systems. Nonetheless, a number of these systems exhibit a tentacle like appearance that can be eerie or unnerving to a subject.

Certain examples of the prior art use semi-rigid bands or straps placed transversally around (along the horizontal circumference of) the head to help maintain electrode contact. Some of these systems use a series of bands placed at various angles relative to a primary transversal band or to each other. These systems are distinguished from elastic nets in that instead of relying on elastic material properties to support a range of head sizes, an adjustment mechanism is used for this purpose. The adjustment mechanism is not limited by material elasticity properties and in some instances can be devised to accommodate a wide range of head sizes.

These semi-rigid circumferential systems have the disadvantage, however, of not supporting a continuous range of position adjustment of individual electrodes. Thus, due to head size and shape variations, the positioning of electrodes is less accurate than desired. In terms of practical and anxiety-reducing design, lead wires are concealed in some semi-rigid systems. Nonetheless, prior embodiments of these systems present as restrictive or restraining to the wearer.

Some head-worn systems are formed of flexible, substantially inelastic adhesive foam and employ integral electrodes. Such systems in the prior art have insufficient elastic tension during use, thus leading to inadequate electrode pressure against the primary hair-bearing regions of the scalp. In addition, if one were to mount electronics to such a system (in order to minimize triboelectric noise and signal travel length, for instance), the system's adhesive foam arms would not have sufficient stability or stiffness to prevent electrode mechanical instability during head movement.

In some examples of the prior art, electrodes attach to a head apparatus by way of helical springs, user-adjustable screws, or pistons that act in combination with a primary apparatus to suspend electrodes or generate reinforcing or counterposing pressure against electrodes. Alternatively, in the prior art, electrodes may attach permanently to a head apparatus. Electrode connection to the skin, in the prior art, typically relies on dry, noncontact (or capacitive), high viscosity gel, structurally durable hydrogel, adhesive gel, conductive paste, or saline interfaces. The ability of an operator or wearer to reposition electrodes is not available in many prior art examples and, where available, is limited in terms of adjustment degrees of freedom and electrode placement flexibility. Further, electrode position adjustment in the prior art relies on mechanisms that are costly to manufacture and complicated to use.

An additional problem in many examples of the prior art is that a sliding action of electrode surfaces across the scalp or hair can occur during placement. This is undesirable in applications where a liquid or low viscosity conductive medium must be used to achieve lower impedance and lower noise, as the medium may be prone to smearing, thus altering the spatial conductive characteristics of the interface. The combination of a conductive medium filling and plunging mechanism can help alleviate smearing, but this type of mechanism often requires repositioning of the operator relative to the wearer and is susceptible to hair interference, complex to manufacture and use, and costly on a per electrode basis.

With respect to electronic systems and interfaces, prior art head mounted systems and their electronic components or counterparts do not enable easy reconfiguration for wired or wireless connectivity. Additionally, battery powered electronic systems in the prior art have insufficient protection from battery-related explosion and fire hazards, relying primarily on electronic and mechanical means of protection. Conventional lithium-based formulation rechargeable batteries are susceptible to explosion and fire risk as a result of combinations of mechanical stresses or failures, electrical stresses or failures, thermal stresses or failures, protection system failures, thermal runaway, dendrite formation, and/or component or manufacturing defects. Further, examples of the prior art do not provide a sufficient means of protection from charging risks while the systems are worn. Charging overvoltage and overcurrent protection failures can lead to electronic system power and front-end failures that in turn may result in significant risk to the wearer or user.

OBJECTS AND ADVANTAGES

Whereas some existing systems are formed as combinations of the above described references, these combinations still suffer from a number of the deficiencies noted.

The following are some of the objects and advantages of the embodiments disclosed herein, categorized for clarity. It should be noted that the following objects, advantages, and inventions are non-limiting, and categories provided are exemplary only and do not limit the scope or applicability of any of the objects and advantages.

General Usability:

The EEG headset is quickly fitted, adjusted, removed, and cleaned by medical and technical non-specialists or those who may lack EEG knowledge, skills, and proficiencies.

The EEG headset and electrode assembly are intuitively fitted on a wearer.

The EEG headset is configured to support detachably attachable electronic system modules, facilitating separation for cleaning, battery charging, system reconfiguration, and other purposes.

Ergonomics:

An advantage of the EEG headset is it is compatible with and accurate across pediatric (child) and adult populations, within a single unit.

An advantage of the EEG headset is that its fit, by way of its supporting and additional elements, is comfortable, ergonomic, and secure but not constraining.

An advantage of the EEG headset is it is partially formed of ergonomically shaped components, such that it does not require use of conformable materials to achieve a comfortable, stable fit.

Appearance and User/Wearer Affect:

An advantage of the EEG headset is it is comfortable, non-restricting, and non-constraining and minimizes headset and procedure related anxieties in wearers, users, and observers.

An advantage of the EEG headset is it may include removable, flat, and anatomically-conforming leads and preferentially does not expose wires, cables, and tubes.

An advantage of the EEG headset is it enables detachable attachment of leads, electrodes, linings, low-tack decals, and other components for the purpose of, for instance, appealing to the gender, age, and/or interests of the wearer and for further reducing wearer anxiety.

An advantage of the EEG headset is it may use ornamental graphic overlays on leads and other visible surfaces to improve wearer acceptability and reduce wearer anxiety, particularly in pediatric populations.

Safety and Contamination:

An advantage of the EEG headset is it is formed to provide low contamination and microbial transfer risk, including that stemming from reposable and non-disposable components.

An advantage of the EEG headset is that it provides a low risk of soiling and contaminating the operator (with conductive mediums, biological contaminants, and other substances), relative to other low impedance EEG systems.

An advantage of the EEG headset is it does not use elastic caps, elastic bands, or natural or synthetic materials that are difficult to clean or are prone to contamination risk in non-disposable form.

An advantage of the EEG headset is it reduces risk, relative to conventional EEG systems, of detachment-related safety hazards.

An advantage of the EEG headset is it reduces risk, relative to conventional lithium-based rechargeable systems, of fire and explosion stemming from battery and power failures.

An advantage of the EEG headset is it prevents charging, and associated charging-related safety hazards, when worn.

An advantage of the EEG headset is it permits wireless or inductive charging of detachably attachable electronic system modules, facilitating, for example, charging connection and prevention of liquid and fluid ingress into charging ports.

Signal Performance:

An advantage of the EEG headset is it may include driven leads, lead shielding, and optional active leads to reduce electromagnetic induced noise to below that achievable in non-shielded EEG systems.

An advantage of the EEG headset is it may include lead structures that reduce motion/triboelectric noise to below that achievable in conventionally-leaded EEG systems.

Sensors and Conductive Mediums:

An advantage of the EEG headset is it facilitates inter-electrode impedances of below 5,000 ohms with minimal or no skin abrasion.

An advantage of the present method of use and cost-effective electrode assembly is prevention of conductive medium smearing during placement, adjustment, and removal.

Placement Ease of Use and Accuracy:

Also disclosed are self-supporting electrode leads with four or more degrees of freedom in their adjustability relative to their nominal position, realized cost effectively and with reduced manufacturing burden.

An advantage of the self-supporting, articulable electrode leads is that they enable accurate electrode placement on the wearer.

An advantage of the electrode placement/locator system that incorporates an optional measurement feature, is that it is simple to use, minimizes user-related error, ensures accurate and reliable electrode placement on a subject, and may be used for headset or other anatomically-associated object positioning or positional marking on a subject.

Modularity:

Disclosed is an adaptable EEG headset that may be configured with a plurality of electronic system types, for example, EEG and non-EEG, active and passive, local and remote processing, local and remote storage, and wired and wireless communication, among other system types.

An advantage of the EEG headset is that it is readily adaptable to different electrode types, conductive mediums, and configurations.

Additional Objects and Advantages:

Disclosed is an EEG headset that does not occlude the ears, in cases where in-ear or on-ear transducers are not needed in use.

An advantage of the present EEG headset is that it reduces per use operating costs relative to conventional medical EEG systems of similar low impedance capability.

These and Further Objects and Advantages Will Become Apparent in the Ensuing Description and Drawings.

A system for measuring brain electrical activity has conforming shaped lateral supports, located predominantly over the temporal fossae, as a mode of stabilization on the head, one or more electrodes for conductive interfacing with the wearer, and optional thin flexible leads. The system is configured for stability and comfort over a wide range of head sizes and shapes and is designed for efficient, cost-effective reconfiguration of electrode locations and quantity. The lateral support structure may include one or more central cutouts or depressions to enhance fit compatibility and reduce heat generation, and may accept disposable interface linings for additional comfort and stability. The system is made to be compatible with disposable, reposable (having a recommended limited number of uses), and non-disposable electrodes. A plurality of optional integral, counterposing pressure tabs may accept the electrodes. Connection components facilitate the quick insertion and removal of the electrodes and flexible leads. Electrodes for use on the hair bearing scalp region may optionally be used with, or manufactured to include, a low-viscosity wet-gel conductive medium, an integrated circumscribing low-tack adhesive optimized for hair compatibility and system stability, and/or a removable adhesive protection layer.

The system is formed to be substantially self-locating on the wearer but may include or be used with a measurement system for placement verification and improved placement accuracy. The measurement system, which may include one or more measurement strips and/or placement templates, is used to accurately locate anatomical landmarks and reference points, enabling accurate placement of electrodes and other components of the system on the wearer.

The system includes or interfaces with an electronic system for signal acquisition, signal measurement, and electrode impedance measurement. The electronic system optionally includes a wireless transceiver. Supplementary methods of system stabilization on the head may be provided, where necessary, and may include one or more of an adhesive-lined film, conformable material lining, elastic band, and expanding support structure. Additional methods of enhancing compatibility with head size and shape may include incorporating one or more of a spring or spring hinge for secondary lateral pressure, inwardly inclined lateral support resting angle, multiple rotation axes lateral support, selectable thickness conformable interface lining, and headband length adjustment. Further provision is made for lining contact surfaces of the system with a textured material or pattern that inhibits microbial survival and transfer and that beneficially increases frictional engagement between the system surfaces and the wearer's skin, hair, and/or scalp.

In one embodiment, rotation of lateral support assembly 120, 130 is improved in one or both of the anterior and posterior directions. In one embodiment, improvement in the rotation of lateral support assembly 120, 130 is achieved by the inclusion of a spring and/or pin mechanism attached to the interface of lateral support assembly 120, 130 and adjustment band 252. In a separate embodiment, improvement in the rotation of lateral support assembly 120, 130 is achieved by selecting the hinge assembly to be a dual-rotation-axis hinge, for example, selecting the dual-rotation-axis hinge as hinge assembly 140. In a further embodiment, lateral support assembly 120 and/or lateral support assembly 130 is replaced with an alternative support mechanism or with a support mechanism housing an active electronic function.

In lieu of or in addition to the disclosed electrodes and their supporting and associated elements, additional embodiments of the system are designed to accept any type of biological or non-biological sensor or emitter, including but not limited to that of an oxygen saturation sensor, respiratory sensor, proximity sensor (for automated powering on and off and other uses), optical sensor, visible and non-visible light spectrum sensor, chemical sensor, resistance sensor, temperature sensor, heart rate sensor, ocular sensor, gaze sensor, nystagmus sensor, audio transducer, or electrical stimulator.

In one embodiment, a system for connecting alternative electrodes or sensors to the EEG headset is provided. Substituted electrodes may interface, for example, by direct connection to the EEG headset or by an intermediary lead adapter. Connection via the intermediary lead adapter may be by a standard port or a special-purpose electrode/sensor port located on the EEG headset proximal to the sensing location.

The system may include a means of measuring and tracking head, eye, and body motion by incorporating a motion or tracking sensor. Motion measuring and tracking may be integrated into the electronic system or may otherwise interface with the electronic system. For instance, a multi-axis sensor, such as that of a nine-axis motion sensor device, may include, in one embodiment, one or more accelerometers, gyroscopes, or compass sensors and may transmit measurement and tracking analog signals or digital data for reception by portions of the electronic system or by a monitoring, processing, and/or recording system.

BRIEF DESCRIPTION OF THE FIGURES

For purposes of understanding the following brief and detailed descriptions of the drawings, it is noted that the directions "left" and "right" refer to anatomical left and right sides of the wearer, and as such, features described on left and right sides may not correspond with left and right sides of the drawing sheets.

FIG. 26 details an exemplary method for quickly and accurately locating the EEG headset on a wearer, in an embodiment.

DETAILED DESCRIPTION OF THE FIGURES

Figure 1:
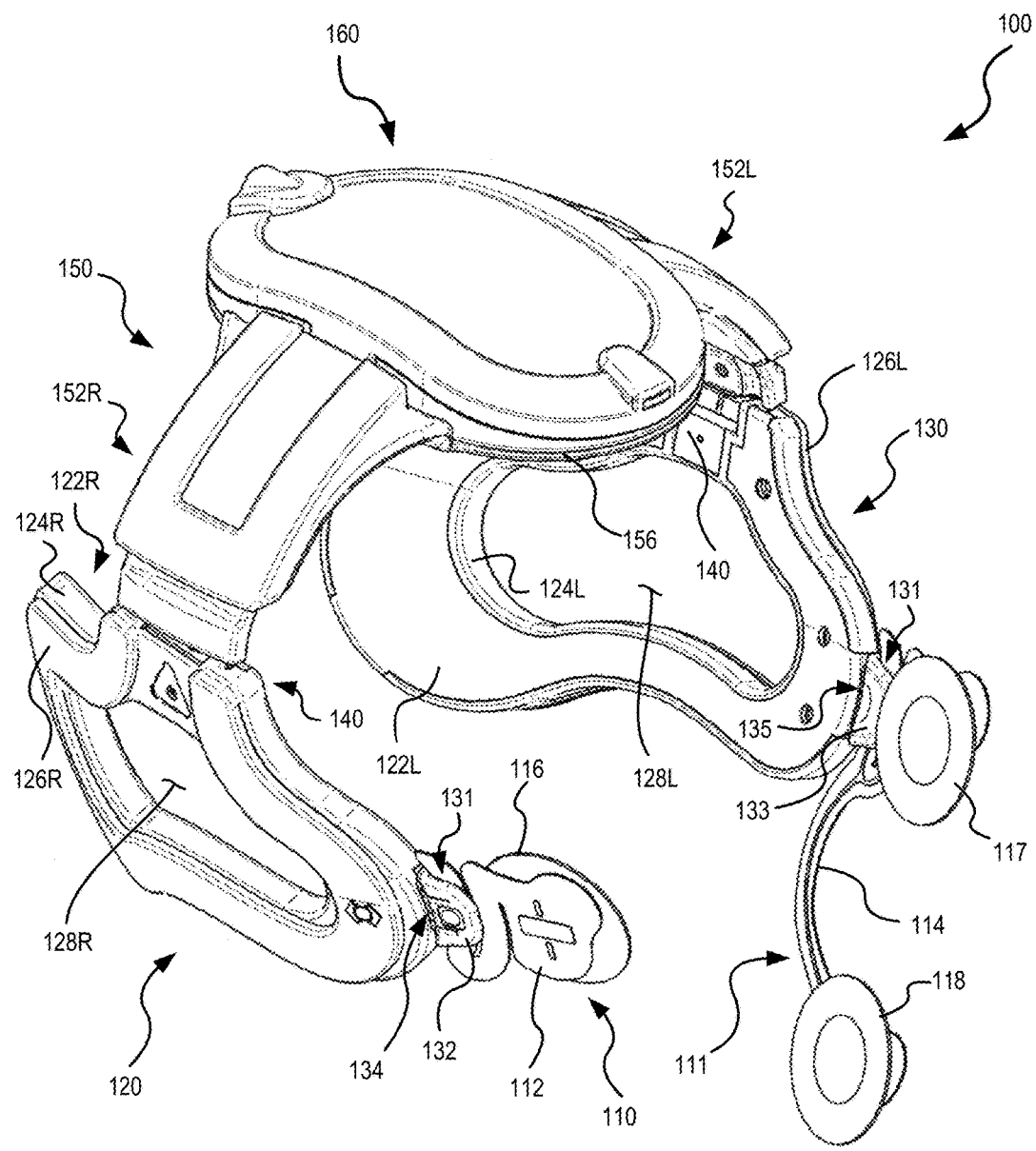
FIG. 1 is a perspective view of an exemplary EEG headset with left and right electrodes included, in an embodiment.
Figure 2:
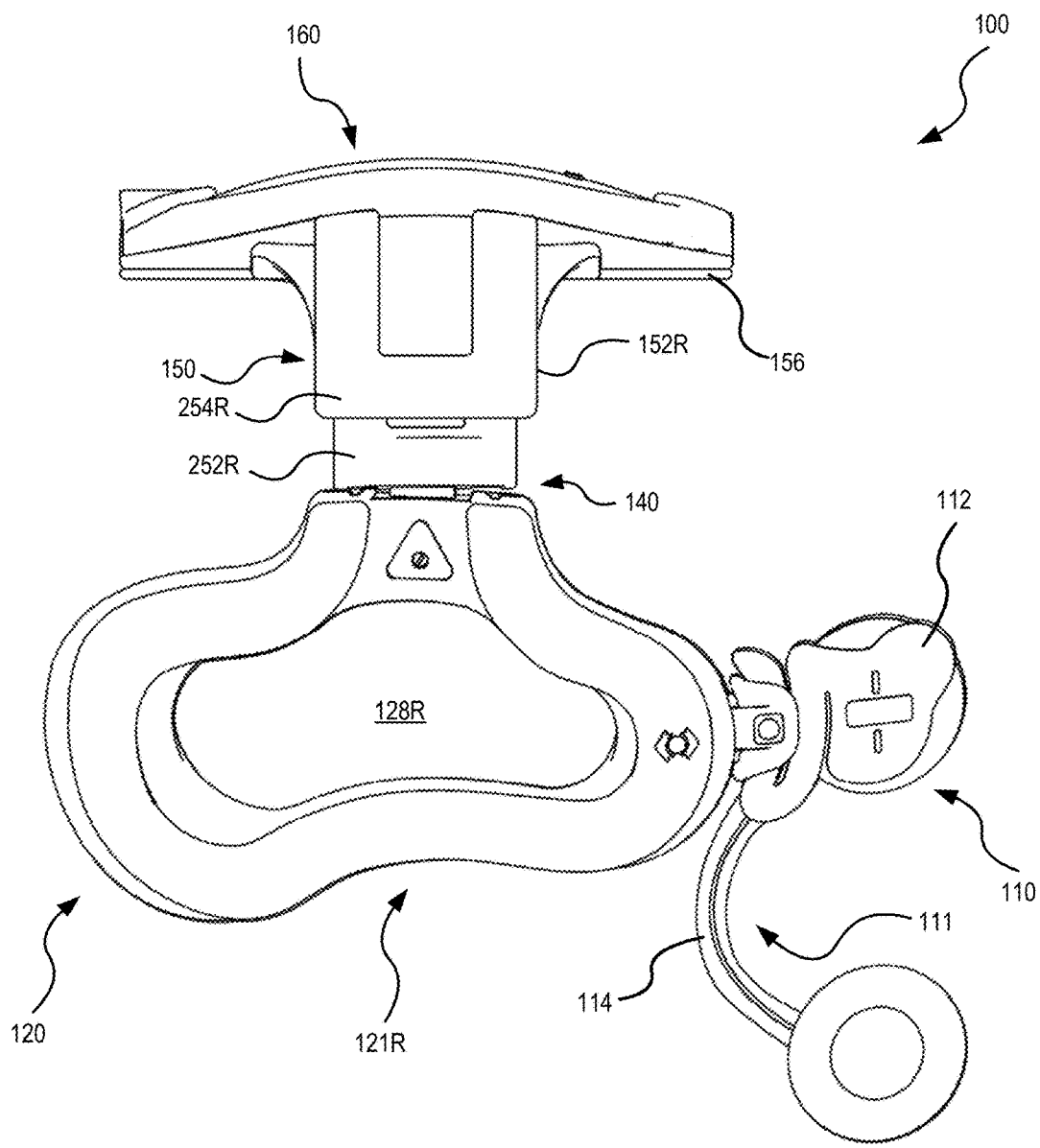
FIG. 2 is a left side view of the EEG headset of FIG. 1.

An EEG headset 100 is shown in FIG. 1 in a first perspective view and in FIG. 2 in a side view. EEG headset 100 includes a right lateral support assembly 120, a left lateral support assembly 130, two spring hinge assemblies 140, a headband assembly 150, an amplifier assembly 160, and an electrode/lead assembly 110, 111. In FIGS. 3-8, EEG headset 100 is shown with portions of the electrode/lead assembly 110, 111 removed for clarity of illustration. FIGS. 1-8 are best viewed together in consideration with the following description.

Lateral support assemblies 120, 130, acting in combination with related parts to be described below, are formed to enhance and/or maintain, within a single unit, wearer comfort, stability, and fit across a wide age range. Additionally, lateral support assemblies 120, 130 may be formed to conceal lead paths, provide entry points for electrodes and leads, physically support visible lead extensions, and provide mechanisms for detachable attachment (hereinafter also referred to as temporary or removable attachment) of lead plugs, among other functions.

Right and left lateral support assemblies 120, 130 are formed of one or more contoured and predominantly rigid polymer layers. Right and left lateral support assemblies 120, 130, as shown, include main lateral supports 122R, 122L, inner lateral supports 124R, 124L, and outer lateral supports 126R, 126L, affixed by screw, snap fit, key-lock, or other fastening method. Lateral support assemblies 120, 130 may also include one or more electrode lead jacks 134, 135.

In some embodiments, lateral support assemblies 120, 130 may be formed to comfortably and securely rest on head surface regions of limited anatomical variability and/or limited muscle movement. For example, lateral support assemblies 120, 130 of EEG headset 100 are uniquely shaped and sized to rest laterally and above the ears, over the temporal fossae. With respect to feature variation within an anatomical region, the temporal fossae have reduced variability compared to other extracranial regions that may potentially support a head apparatus. For example, greater variability exists in the auricular, circumaural, mastoid process, and zygomatic process anatomical regions than in the temporal fossae. Additionally, the temporal fossae are less prone to muscle motion during ordinary head movement, vocalization, and facial expression than regions inclusive of the inion, posteroinferior skull, forehead, masseter, orbicularis oculi, and subaural musculature, as examples. Although a major portion of the temporalis muscle resides within the temporal fossa and this region is susceptible to myogenic electrical activity, the magnitude of temporalis muscle movements is limited centrally within the temporal fossae.

Figure 19:
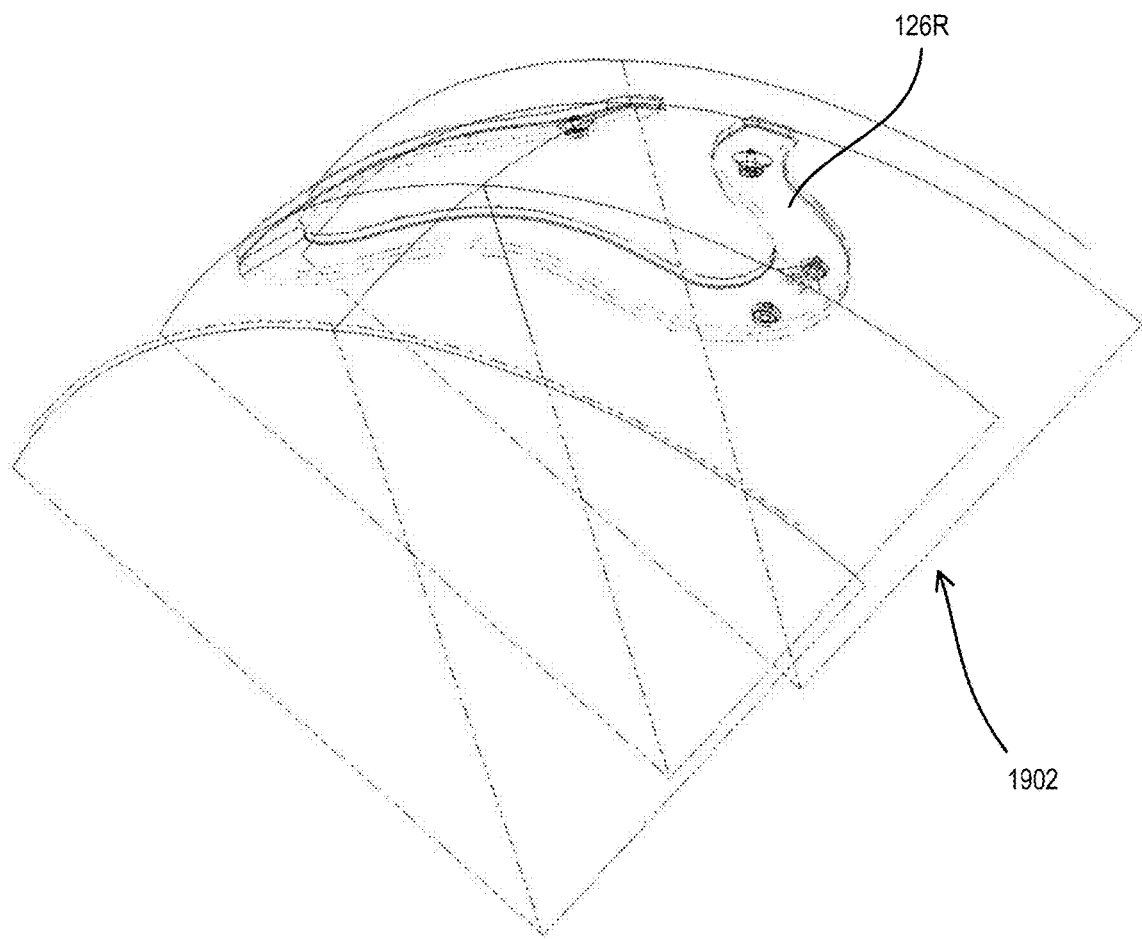
FIG. 19 shows an exemplary curvature model for an outer lateral support of an EEG headset, in an embodiment.

In some embodiments, human head size, shape, and other biometric data, in the form of means and standard deviations across a specified age range, may be used to optimize the size and anatomically conforming curvature of the lateral support assemblies. Head size and shape data may be further used to ensure anatomical stability and non-impingement across individuals within one or more biometric ranges. In an embodiment, the anatomically conforming curvature may be designed as a compound variable curvature by varying curvature amount along a plurality of anatomical directions. For example, shape forming curves may be selected to provide non-impinging wearer comfort and stability in anterior-posterior and superior-inferior directions. See, for example, exemplary curvature model 1902 of right outer lateral support 126R, FIG. 19. Further, width and height of the lateral support assemblies may be selected to optimize compatibility and comfort across desired biometric ranges. For example, width, height, and anatomically conforming curvature of EEG headset 100 are selected for compatibility over a head size range that spans two standard deviations below an age six mean head size to two standard deviations above an adult mean head size. Lateral support assemblies 120, 130 for example measure, in side view, approximately 107 mm in width and 70 mm in height. It should be noted that alternative widths, heights, anatomically conforming curvatures, and/or biometric basis data may be selected without departing from the scope herein. It should likewise be noted that although lateral support assemblies 120, 130 are shown as fitting over the sides of a wearer's head, the shape, size, and contour of support assemblies may be adapted to be worn at alternative regions of a wearer's head. Additionally, although shown and described as fitting across the top of a wearer's head, headband assembly 150 and amplifier assembly 160 may be adapted to be worn toward the rear or front of a wearer's head by altering the angle between headband assembly 150 and lateral support assemblies 120, 130.

In addition to providing comfort, stability, and compatibility, a further advantage of anatomically conforming supporting members, placed over low-anatomical-variability surface regions, is that cushions or conformable linings may be omitted if desired. Furthermore, if linings are used, they may be formed of much thinner materials than would otherwise be required for comfort, stability, and compatibility.

In one embodiment, stabilization of lateral supports 120, 130 is improved using low-tack, hair-compatible adhesive on one or more electrodes or patient interface surfaces of EEG headset 100. In a further embodiment, lateral support assemblies 120, 130 are spring mounted (via a spring hinge or other spring apparatus) to assist in isolating electrode-bearing regions from motion occurring at the lateral support assemblies.

In another embodiment, one or more semi-rigid extensions may be placed on the lateral support assembly, for example on lateral support assembly 120, to aid in headset retention or to provide an ear or mastoid electrode contact point.

In some embodiments, system supporting elements, such as lateral support assemblies 120, 130, may include one or more central cutouts or depressions in order, for instance, to enhance fit compatibility, reduce cost, improve aesthetics, and/or reduce wearer heat and perspiration buildup (due to thermal insulation and skin occlusion). In FIGS. 1, 2 and 3-8, lateral support assemblies 120, 130 are depicted each with a single cutout 128R, 128L. A portion or layer of lateral support assembly 120, 130 may optionally include a softer polymer for improved wearer comfort and conformance. An adhesive-backed hook and loop system may be used to secure a compressible, breathable lining to any wearer interface surface, such as on the wearer interface surface of lateral support assembly 120, 130.

Figure 3:
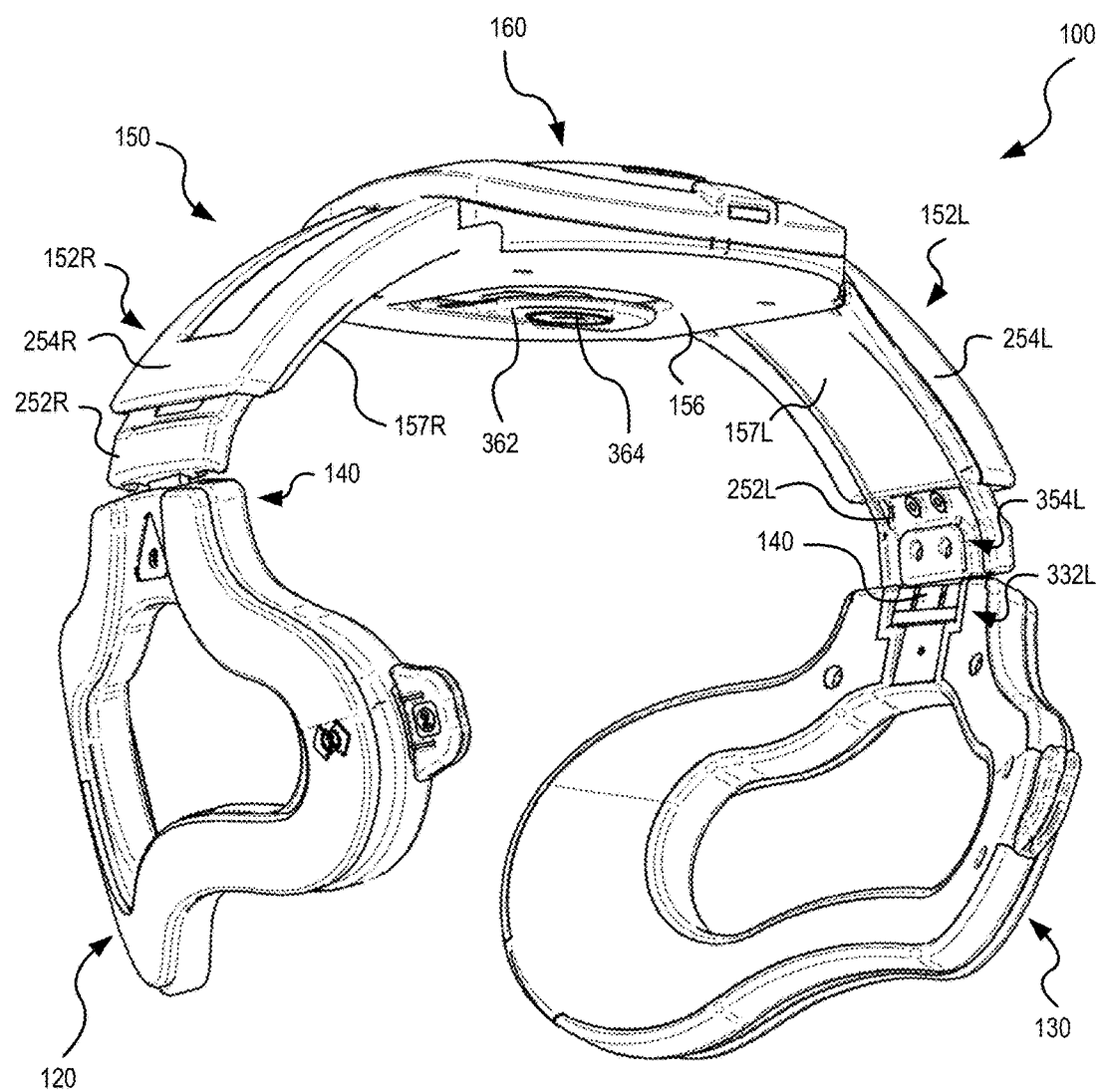
FIG. 3 is another perspective view of the EEG headset of FIG. 1 with left and right electrodes removed.
Figure 4A:
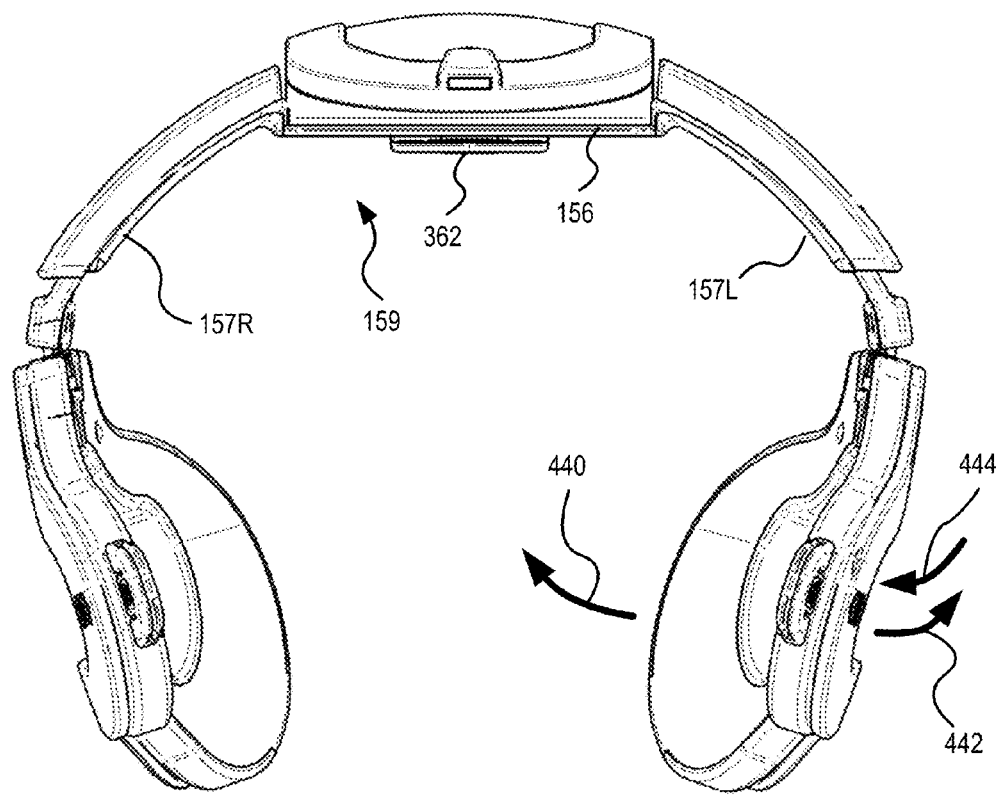
FIG. 4A is a front view of an exemplary embodiment of the EEG headset of FIG. 2 with its headband aspect shown in a flexed state.
Figure 4B:
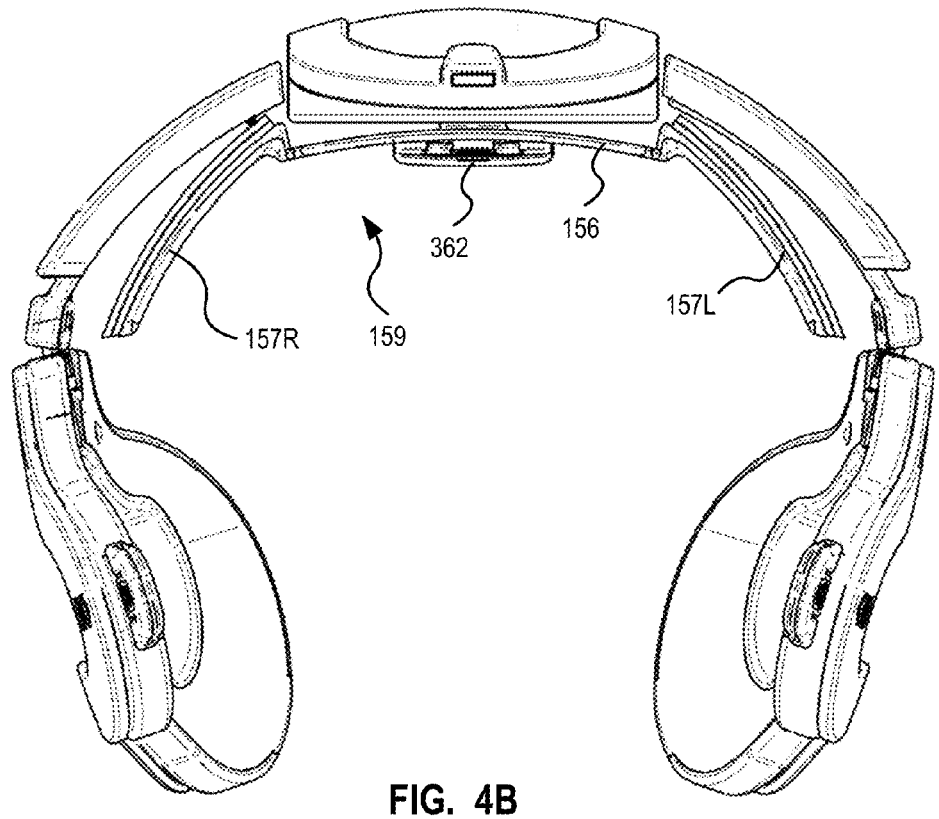
FIG. 4B shows the EEG headset of FIG. 4A in a partially assembled state, with its headband aspect in a relaxed, nominal state.
Figure 5:
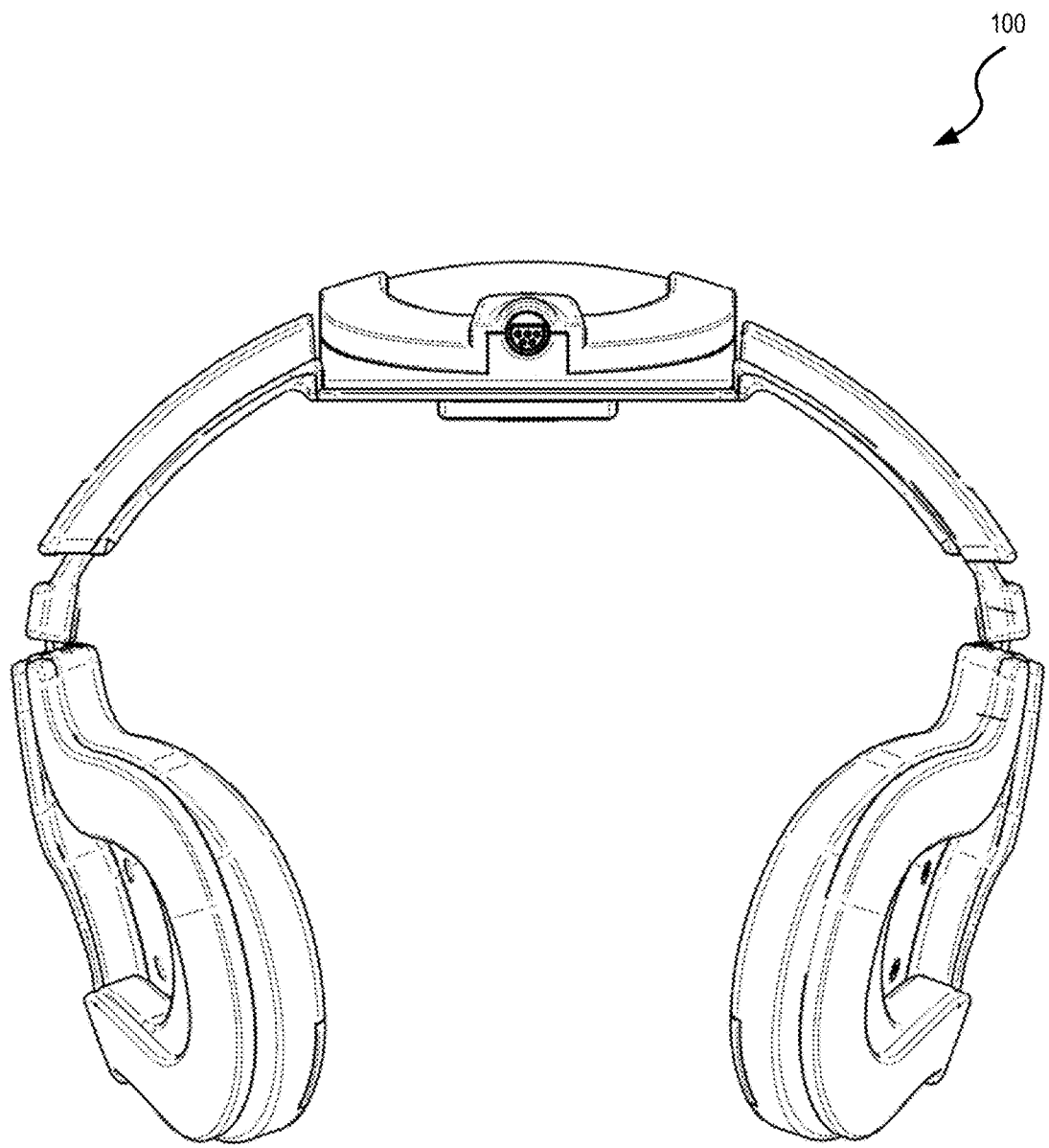
FIG. 5 is a rear view of the EEG headset of FIG. 2.
Figure 6:
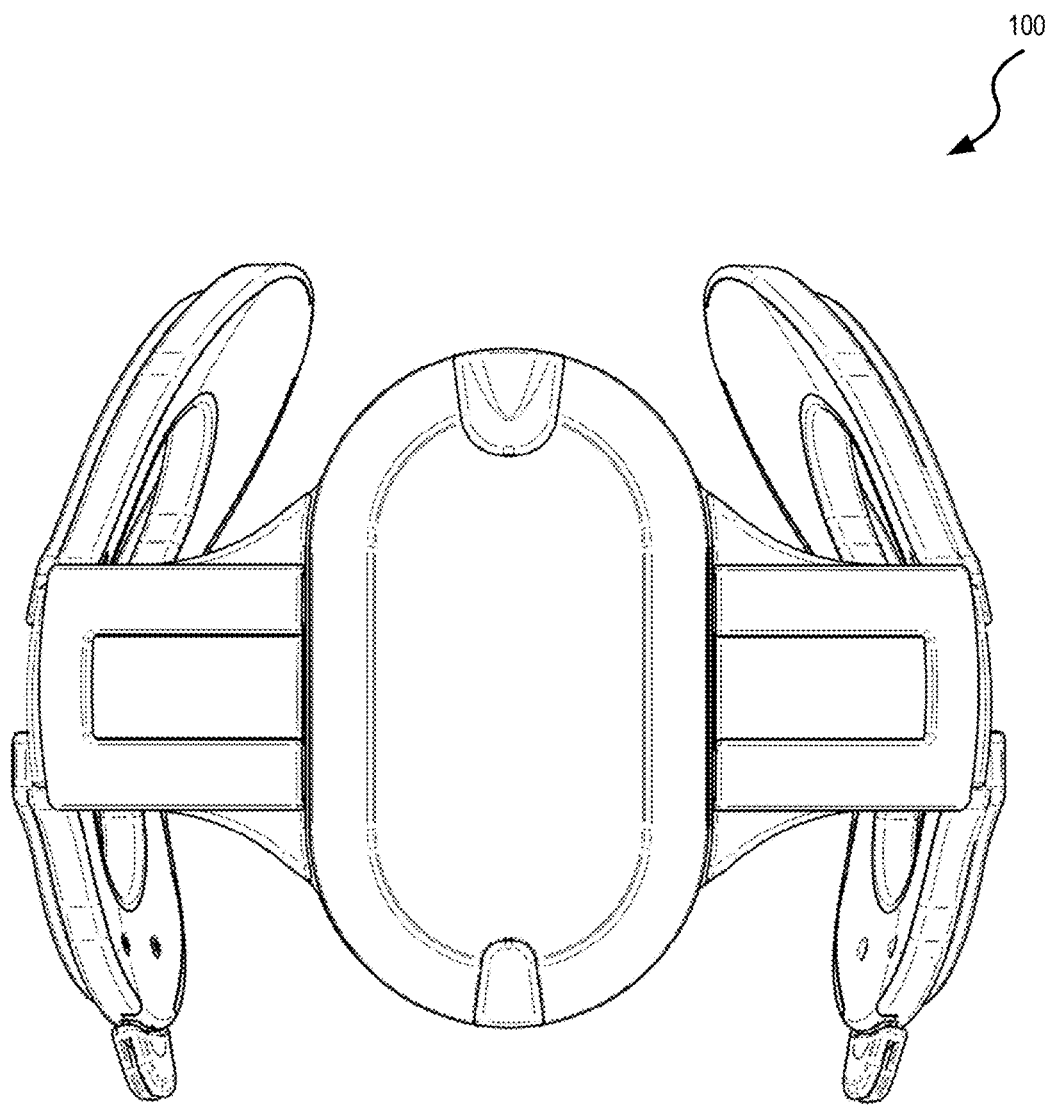
FIG. 6 is a top view of the EEG headset of FIG. 2.
Figure 7:
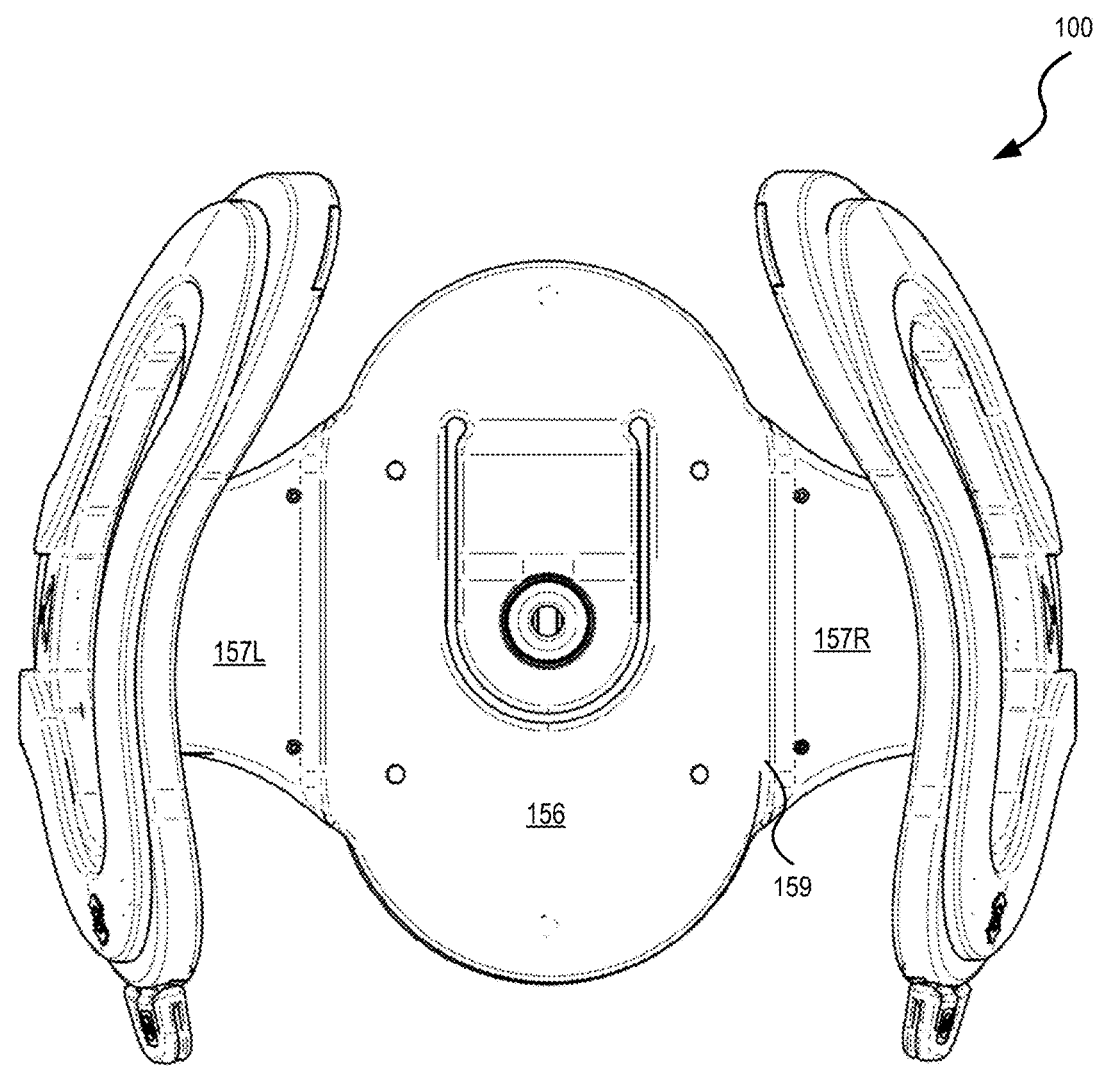
FIG. 7 is a bottom view of the EEG headset of FIG. 2.

As shown in FIG. 3, spring hinge assembly 140 is configured with a conforming hinge slot/depression 332L in lateral support assembly 130 and is secured by, for example, screw connection. Although not shown in FIG. 3, lateral support assembly 120 is also formed with a conforming hinge slot/depression for accepting spring hinge assembly 140. Spring hinge assembly 140 includes one or more internal springs. In an embodiment, spring hinge assembly 140 is constructed such that lateral support assemblies 120, 130 swing through an inward arc 440 (FIG. 4A) of a first range, for example, 90 degrees inward from a nominal unfolded position, to a folded position (not shown). In addition, spring hinge assembly 140 is constructed such that lateral support assemblies 120, 130 may swing through an outward arc 442 (FIG. 4A) of a second range, for example, 20 degrees outward from the nominal unfolded position. In some embodiments, hinge assembly 140 is formed with one or more springs acting in the second range to apply a spring force in a direction 444 (FIG. 4A) toward the nominal unfolded position shown in FIG. 4. When worn, the spring force in the second range generates pressure to assist in comfortably securing EEG headset 100 to the wearer's head. Alternative embodiments may incorporate alternative types of spring hinges with, for example, differing ranges and/or different spring hinge attachment methods or features. Still other embodiments may utilize a springy member in place of spring hinge assembly 140. Still other embodiments may integrate a springy member into lateral support assemblies 120, 130 and right and left adjustment bands 252R, 252L. In embodiments using a spring or springy member, support conformance for smaller head sizes may be improved by selecting a nominal unfolded position wherein a support lower portion is inwardly directed relative to an upper portion or hinge point.

The following description is best viewed in combination with FIGS. 1, 2, 3, 4A, 4B, 7, and 8. Headband assembly 150 includes a headband 159, two headband covers 254R, 254L and two adjustment bands 252R, 252L. For reference, curved arms 152R, 152L refer to curved extension regions of headband assembly 150. In an embodiment of EEG headset 100, spring hinge assemblies 140 attach to headband assembly 150 by insertion into conforming hinge slots 354R (FIG. 8), 354L (FIG. 3) of adjustment bands 252R, 252L and are secured, for example, by screw connection.

Headband 159 includes right and left headband extensions 157R, 157L connected to a central amplifier platform 156. Right and left headband extensions 157R, 157L may be formed integral to amplifier platform 156, as shown in FIGS. 1, 2, and 3-8, or may be formed separately and fixed together during the manufacturing process. Headband covers 254R, 254L attach to headband 159 through slide action along lipped rails of headband 159, this attachment forming semicircular cavities within curved arms 152R, 152L. The cavities partially house shape-conforming adjustment bands 252R, 252L that may slide within the cavities to enable adjustment to accommodate a plurality of head sizes. Stop detents (see a stop detent 855, FIG. 8) on headband covers 254R, 254L and corresponding protrusions (not shown) on adjustment bands 252R, 252L act to prevent adjustment bands 252R, 252L from escaping from headband assembly 150. Adjustment bands 252R, 252L form a wide inner groove or flexing slot 256, which may be used to accommodate the flexing of internal cables or flex circuit leads. In one embodiment, a cable is able to freely flex inside flexing slot 256. In an alternative embodiment, a flex circuit is formed as a sinusoidal, triangular, or similar two-dimensional pattern to enable flexing within flexing slot 256. In still another embodiment, a flex circuit is formed with small folds that extend out of the primary two-dimensional plane of the flex circuit to enable flexing within flexing slot 256.

A detent spring cavity (not shown) in adjustment band 252R, 252L may be used to retain a detent spring (not shown). The detent spring is formed of, for instance, a full hard temper stainless steel or other suitable springy material that resists permanent deformation. The detent spring provides stepped resistance by flexing against headband cover 254 detent ridges (not shown) during movement of adjustment band 252R, 252L. In an alternative embodiment, a spring lever or flexible tab is integrally formed on or within the adjustment band, obviating the need for a spring cavity and separate spring.

In an embodiment, headband 159 is formed of a semi-rigid polymer material that flexes to assist in accommodating a wide range of head sizes. Headband 159 is shown in its "flexed" state in FIGS. 1, 2, 3, 4A, and 5-8 and in its "resting" or nominal state in FIG. 4B, where it is depicted detached from headband covers 254R, 254L. When headband 159 is in its "flexed" state, amplifier platform 156, being more flexible than headband extensions 157R, 157L, flexes to a flattened or semi-flattened state, improving extension of an electrode spring tab 362 and improving surface contact of an attached electrode (not shown). Amplifier platform 156, in the embodiment shown, is formed with stiffened front and rear medial regions to prevent flexing in the medial region of the amplifier platform 156. Electrode spring tab 362 is formed integral to amplifier platform 156 and is a ramped flexible member that houses a snap button 364. An electrode, an example of which is electrode 260, may be detachably attached to snap button 364 for signal sensing. In an embodiment, the electrode spring tab houses one or more snap buttons 364 or connectors, accommodating one or more electrodes 260 or other sensors.

In an embodiment, a thin, curved spring is inserted along headband assembly 100 to improve headband 159 tension and to otherwise prevent permanent or creep-related deformation of EEG headset 100. Curved spring wires, bands, plates, or mechanisms may alternatively or additionally be used for this purpose. The curved spring may be formed of, for instance, a full hard temper stainless steel or other suitable springy material that resists permanent deformation. In a further embodiment, a curved spring may be formed on platform 156 and/or spring tab 362 to control spring tension and creep-related deformation along these two areas. Curved springs may be permanently fixed in place or detachably attached such that they may be replaced.

Figure 8:
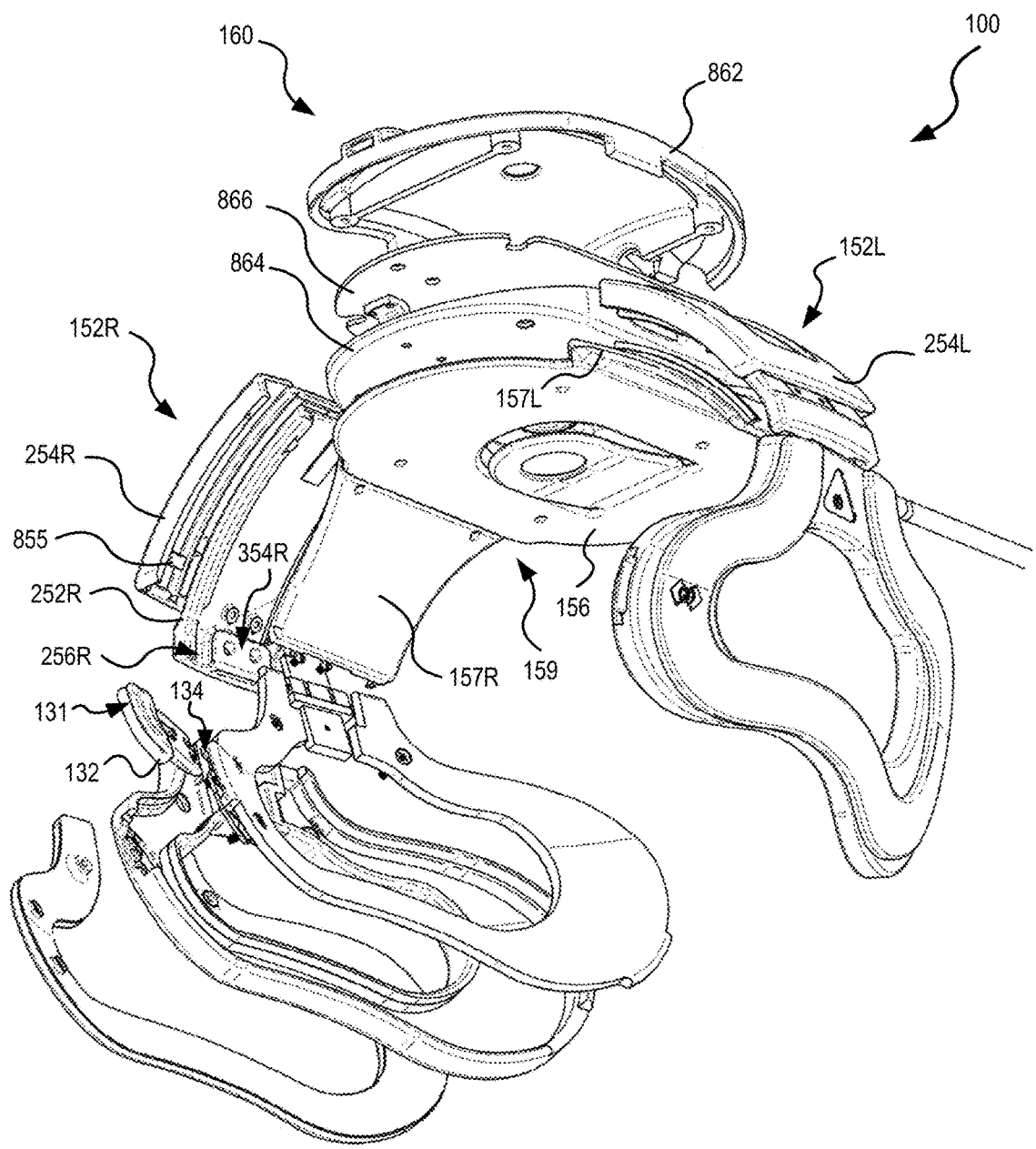
FIG. 8 is a partially exploded view of the EEG headset of FIG. 2.

Amplifier assembly 160, as shown in FIG. 8, includes an amplifier enclosure, formed by the mating of an amplifier upper portion 862, and an amplifier lower portion 864. Although not shown, amplifier assembly 160 may include a range increasing wireless antenna that extends above the top surface of amplifier upper portion 862 to improve wireless transmission signal strength and range.

Secured within the amplifier enclosure is a centrally housed PC board 866. Amplifier assembly 160 may be configured for permanent, semi-permanent, or detachable attachment to amplifier platform 156 or other components of EEG headset 100. In one embodiment, amplifier 160 is attached to amplifier platform 156 by fixation devices, for example, screws, along the medial portions of amplifier platform 156 and amplifier assembly 160. This semi-permanent attachment is suitable when amplifier assembly 160 is not required to be quickly attached or detached in use. Alternatively, amplifier assembly 160 may be detachably attached to headband assembly 150 by, for example, slide locks, two-point click tab locks, vertical friction press-fits, magnet elements, releasable key-lock, or other efficient attachment mechanisms. In some embodiments, a raised lip surrounds portions of amplifier assembly 160, as well as headband assembly 150 and lateral support assemblies 120, 130. See, e.g., FIGS. 1, 2, and 3.

In an embodiment, amplifier assembly 160 of EEG headset 100, FIG. 1, may be configured as a passive amplifier assembly 960 (FIGS. 10-14). Passive amplifier assembly 960 includes an amplifier upper portion 962 and an amplifier lower portion 964, similar to amplifier upper portion 862 and amplifier lower portion 864, respectively. Passive amplifier assembly 960 may optionally include an LED assembly 966.

Figure 12:
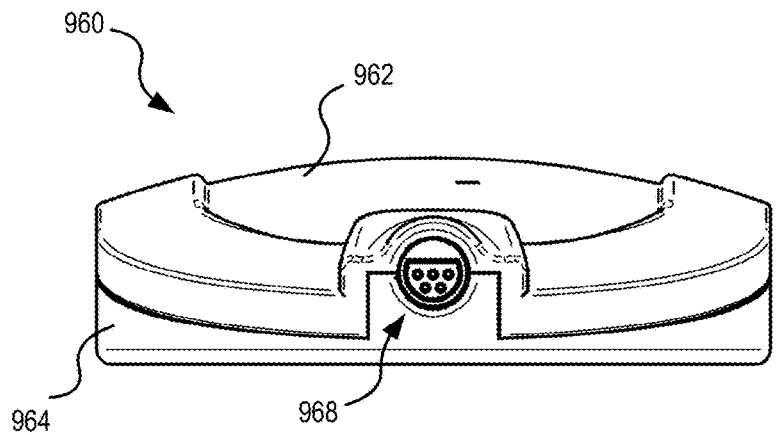
FIG. 12 is a rear view of the amplifier of FIG. 10 with an optional communication port included, according to an embodiment.
Figure 13:
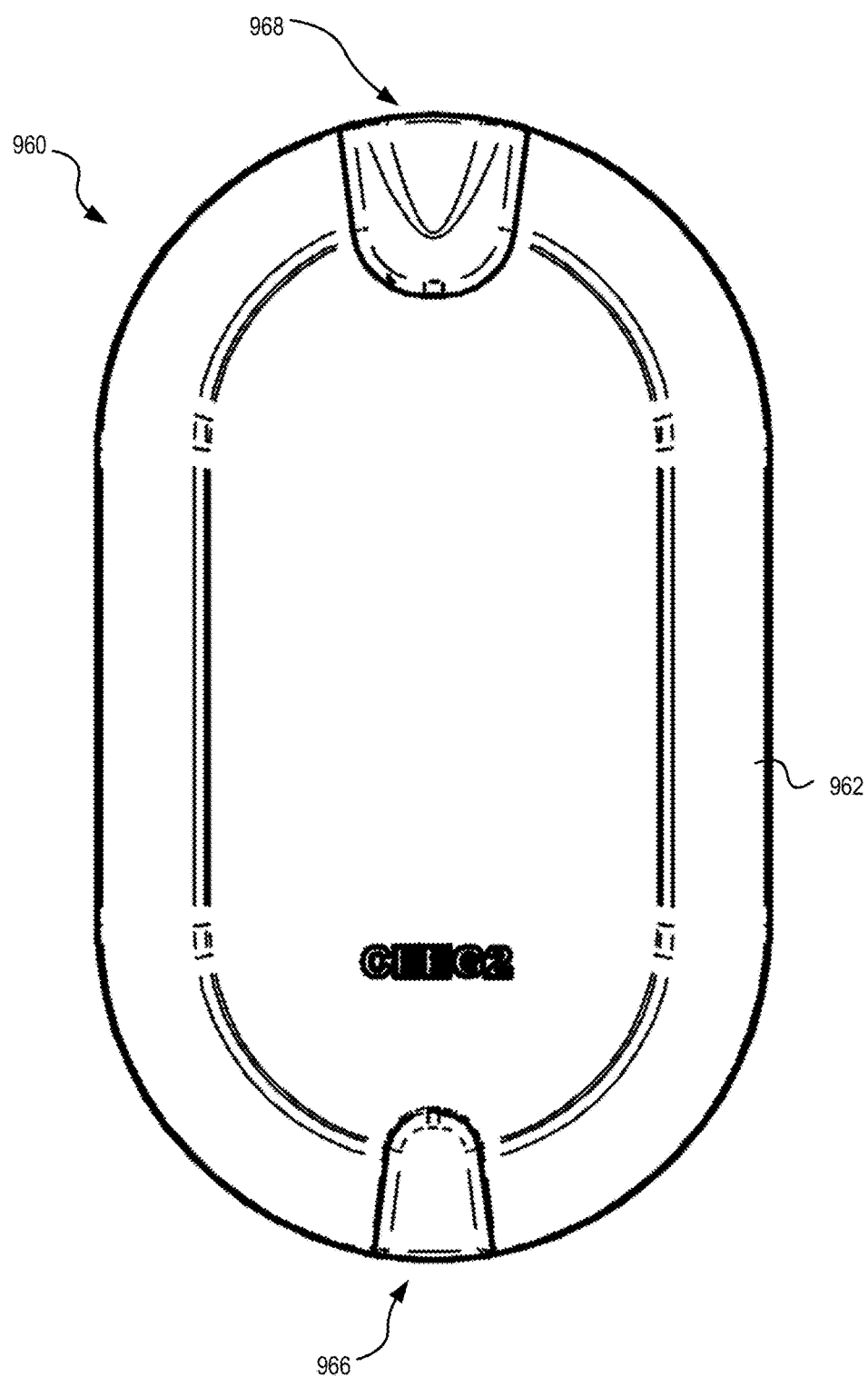
FIG. 13 is a top view of the amplifier of FIG. 10.

Passive amplifier assembly 960 does not house active electronics, but transfers lead signals to an external processing system (not shown) by way of a wired communication cable connected at rear port 968 (FIG. 12).

Figure 14:
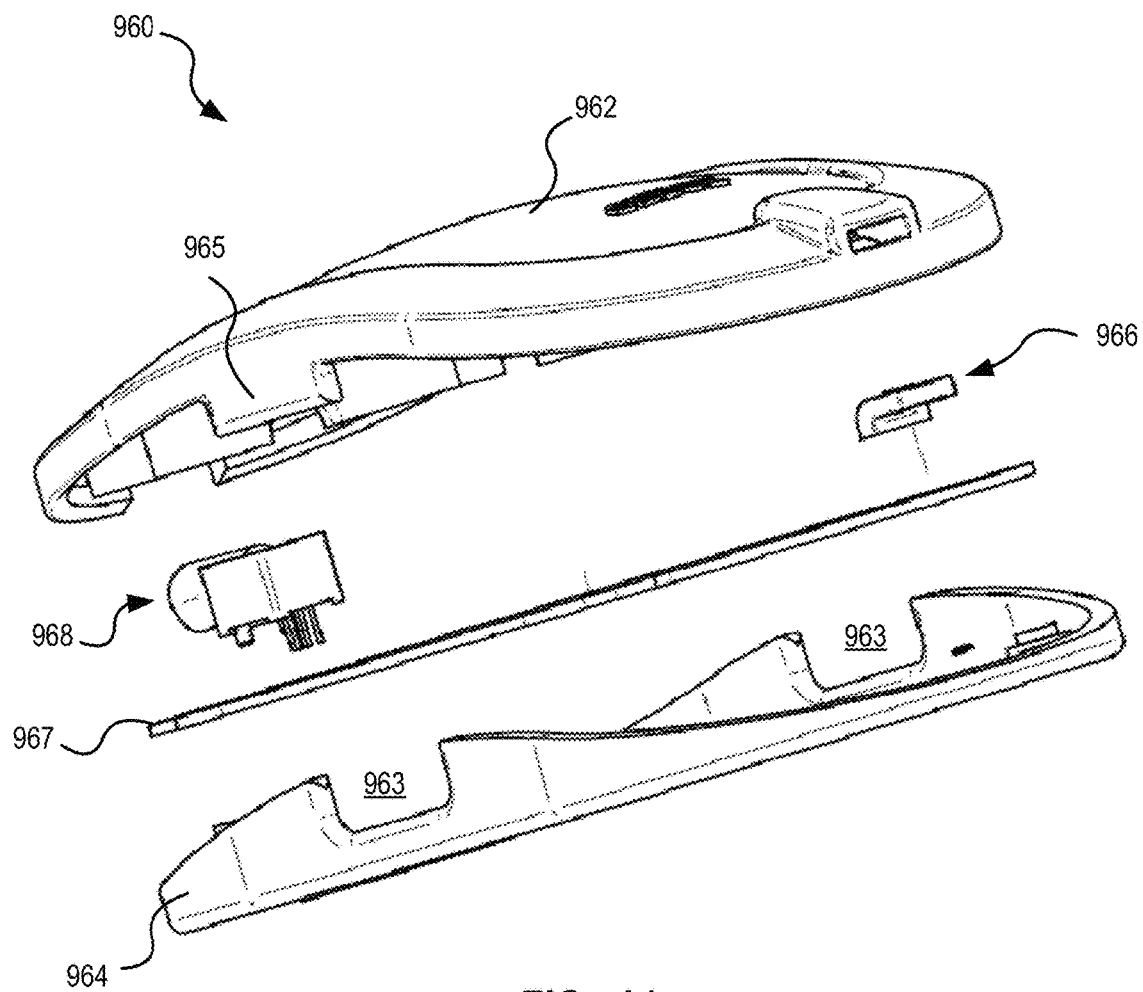
FIG. 14 is an exploded view of the amplifier of FIG. 12.

As shown in FIG. 14, internal leads (not shown) of passive amplifier 960 may pass through a side slot 963, below a side slot extension 965, to an internal cavity formed within amplifier assembly 960. Within the internal cavity, internal leads are provided room for flexion in addition to that provided within curved arms 152R, 152L.

Figure 9:
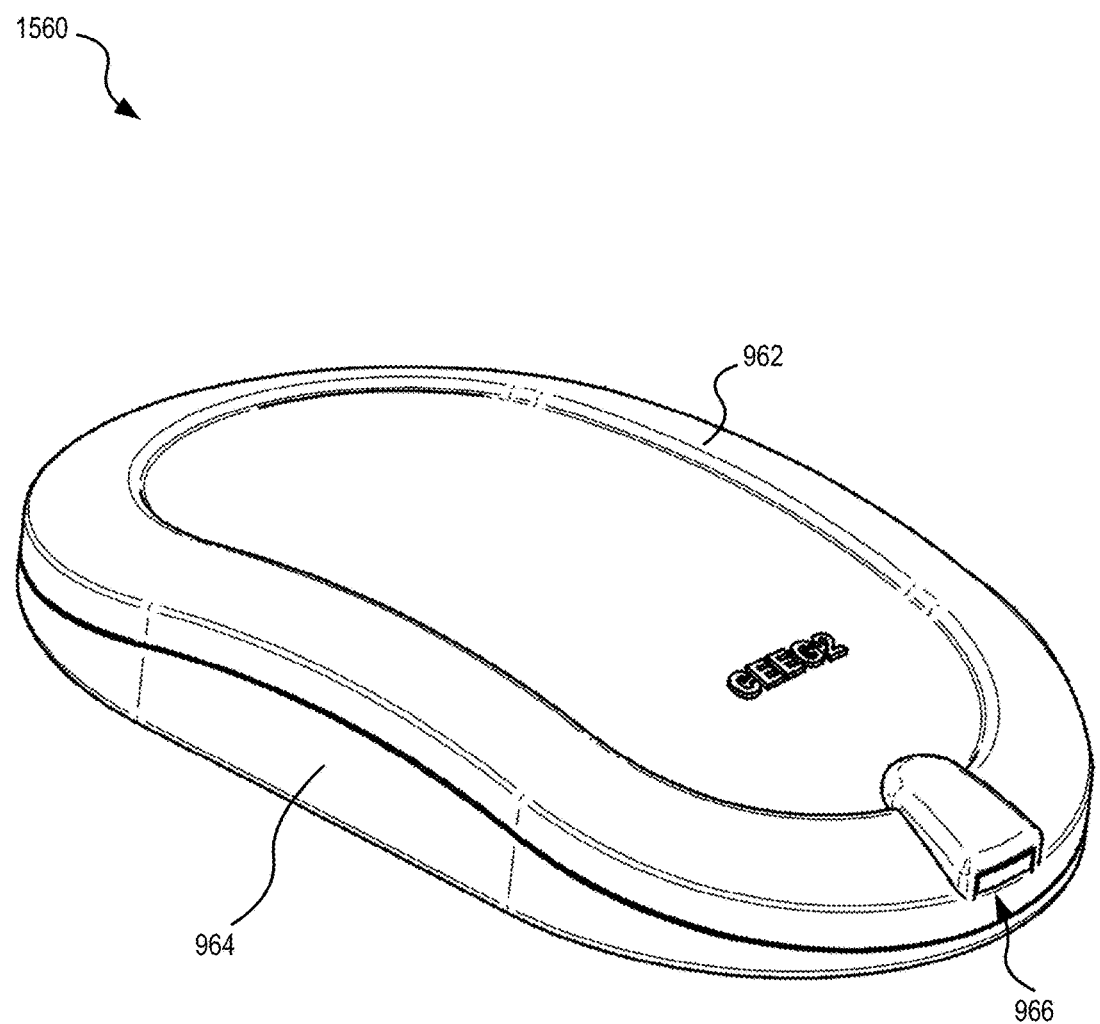
FIG. 9 is a perspective view of an active amplifier of the EEG headset, in an embodiment.
Figure 10:
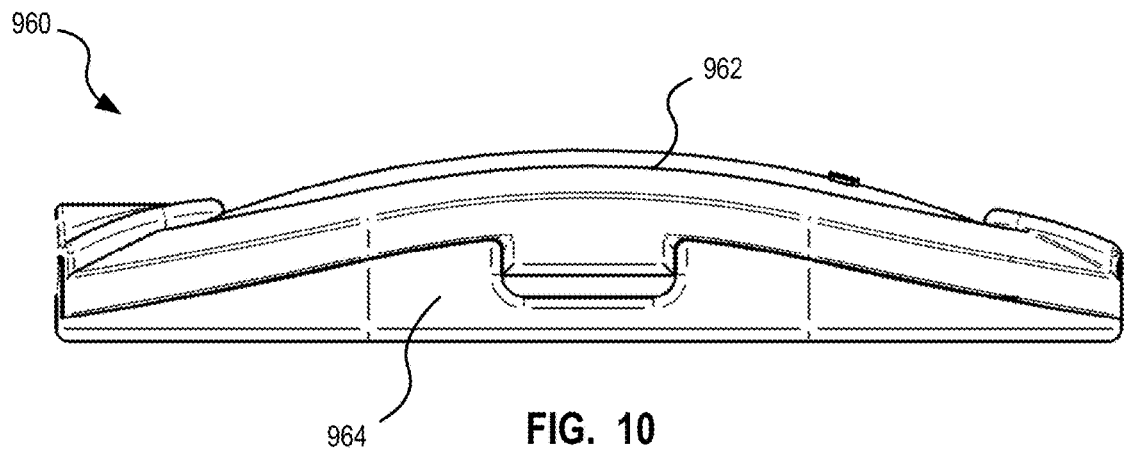
FIG. 10 is a side view of a passive amplifier of the EEG headset, in an embodiment.
Figure 11:
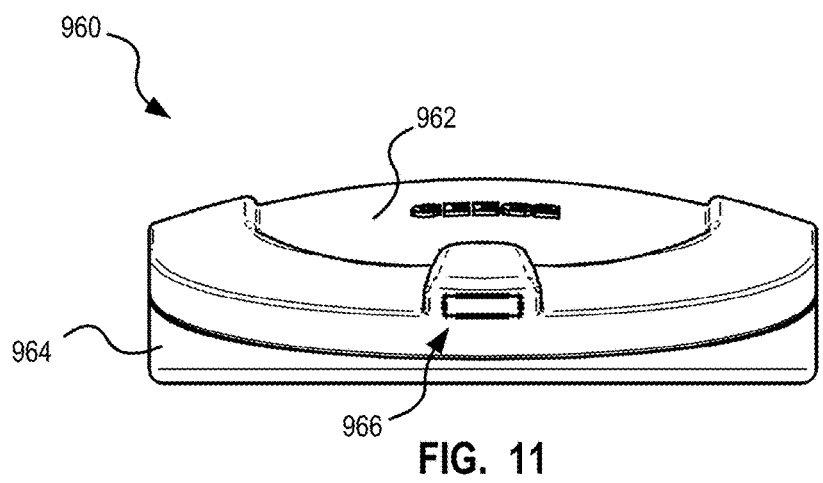
FIG. 11 is a front view of the amplifier of FIG. 10.
Figure 15:
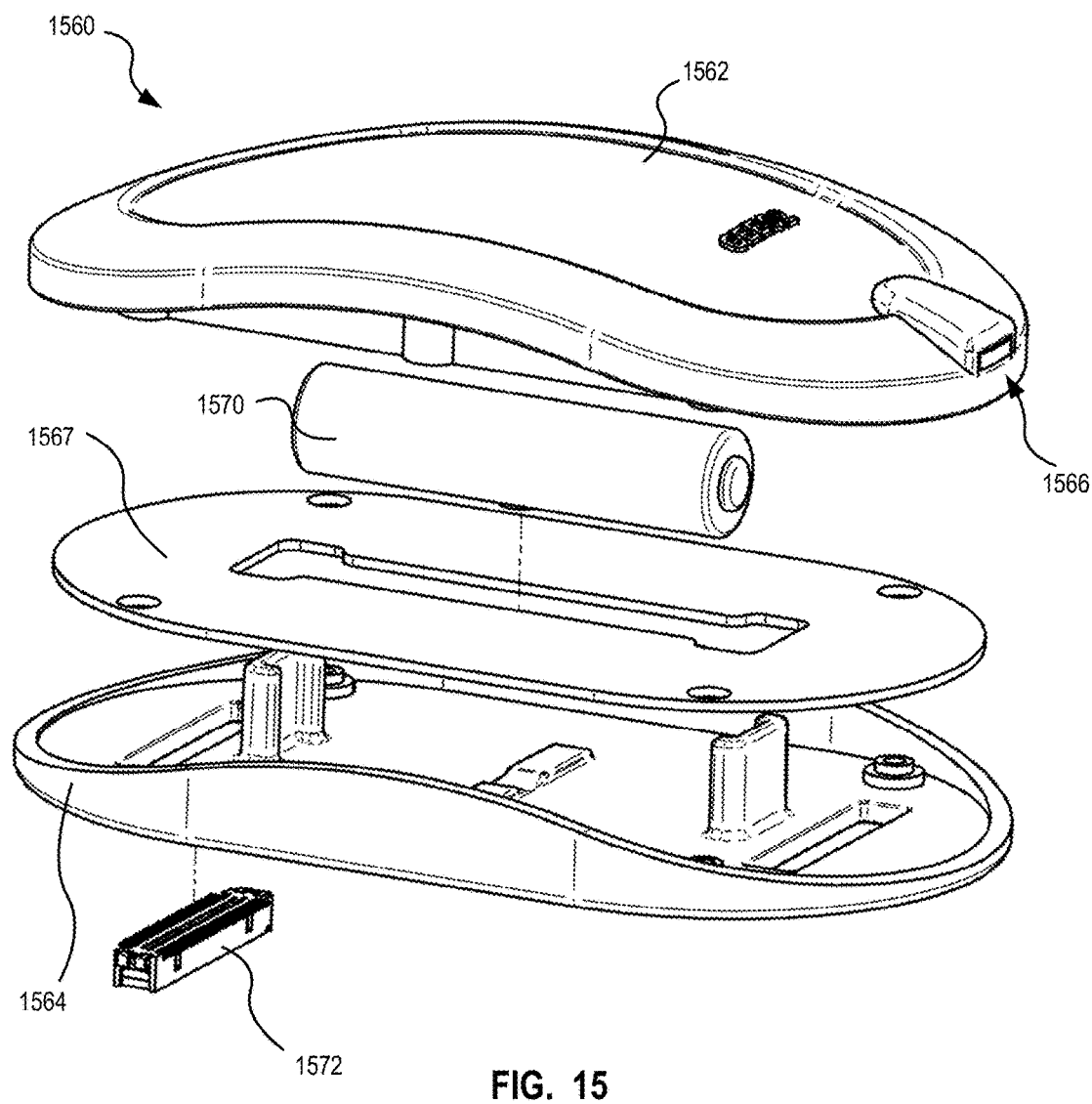
FIG. 15 is an exploded view of the active amplifier of FIG. 9.

Amplifier assembly 160 of EEG headset 100, FIG. 1, may alternatively be configured, in an embodiment, as an active amplifier assembly 1560 (FIGS. 9 and 15). Active amplifier assembly 1560 includes amplifier upper and lower portions 1562, 1564, an electronic system 1567, a battery 1570, and one or more connectors 1572. Internal leads (not shown) pass below active amplifier assembly 1560 and terminate at connector 1572, which is in electrical communication with electronic system 1567. In one embodiment, connector 1572 receives signals from electrodes, for example electrodes 116, 117, 118, via electrically conducting leads, for transport to and processing by electronic system 1567. Electronic system 1567 may include a plurality of processing modules to perform, for example, electrical protection, amplification, filtering, analog to digital conversion, signal measurement, and/or electrode impedance measurement, to name only a few examples. In some embodiments, electronic system 1567 may also include a wireless transceiver for communication with a host system (not shown) for the purpose of, for example, data storage, waveform or parameter monitoring, and additional signal processing.

The signals sensed by EEG headset 100 may be output for various purposes, including, but not limited to, self-monitoring and/or control of software, displays, transducers, mechanisms, and/or devices. In one example, the signals sensed by EEG headset 100 may assist in controlling transport devices and artificial limbs or may assist in selecting objects on a display. In another example, the signals sensed by EEG headset 100 may be self-monitored to assist wearers in learning to control the sensed EEG signals. The signals measured by the system may be evoked responses and potentials in lieu of, or in addition to, background EEG activity.

An impedance signal may be combined with the EEG signal. The frequency of the impedance signal is selected to be outside the primary EEG signal frequency range. During processing, the combined signal may be separated for use in impedance analysis, monitoring, and reporting.

In one embodiment, battery 1570 powers active amplifier assembly 1560 and may be formulated of a lithium iron phosphate ($LiFePO_4$) cathode material that enables safer operation, longer life, and improved power density compared to conventionally specified lithium-based formulations. In an embodiment, battery 1570 is a cylinder of roughly 44.5 mm by 10.5 mm. In separate embodiments, battery 1570 may be replaced by one of any formulation, shape, or size that may be accommodated in the amplifier enclosure or housed external to it. A protruding section of powered amplifier 1560 houses an LED assembly 1566 light pipe for conveying power status and other information. User accessible buttons and additional status lights (not shown) may be located on the top surface of amplifier assembly 1560.

In one embodiment, active amplifier assembly 1560, or an extension thereof, may include one or more proximity sensors to detect if the EEG headset is placed on a wearer. In a further embodiment, the signal received by the proximity sensor signal may be used to control the power status of the EEG headset. For instance, amplifier assembly 1560 may default to a standby or predominantly sleep power mode, then switch to full power mode when a body surface of a wearer is detected within a specified distance from a surface of the EEG headset. In an embodiment, a proximity sensor may be of the capacitive type and its received signal processed to enable discrimination between human bodies and inanimate objects.

In an embodiment, EEG headset 100 may include one or more motion sensors whose output may be analyzed for motion magnitude and other motion-based parameters. In this embodiment, active amplifier assembly 1560 may switch to full power status if motion exceeds a threshold level.

In a further embodiment, proximity and motion sensing may be used in combination for power-related and additional functions. In a further embodiment, power may be configured to remain in standby, sleep, full power, or other mode for a specified length of time after an event or condition is detected, such as that of a proximity, motion, and/or non-motion event or condition.

In one embodiment, active amplifier assembly 1560 may include a charging port (not shown) located on the bottom surface of amplifier lower portion 1564. Due to the location of the charging port, active amplifier assembly 1560 cannot be charged when the EEG headset is worn. To charge active amplifier assembly 1560, it must be detached from amplifier platform 156, which in turn removes the risk of wearer-associated, charging-related safety hazards.

In another embodiment, a wireless charging system (not shown) may be used to power EEG headset 100 or, alternatively, active amplifier assembly 1560. The wireless charging system may include a receiving planar coil (not shown) housed, for instance, in a lower portion of amplifier assembly 1560. The receiving planar coil may wirelessly receive power from an externally housed transmitting planar coil by way of magnetic induction. The transmitting planar coil may be housed in an EEG headset base charging module (not shown) such that charging may automatically commence when EEG headset 100 or active amplifier assembly 1560 is placed within a specified distance from the base charging module. Charging may be controlled by modulation of the power signal in the transmitting planar coil and corresponding demodulation of the power signal in the receiving planar coil. The charging system may be designed to prevent continuous charging power transmission unless transmitting and receiving planar coils are relatively planar-aligned and located within a specified distance. This assures a specified power transfer efficiency or coupling factor is achieved prior to continuous wireless power transmission. The charging system may be designed such that a minimum charging distance of, say, 5 mm is selected and the distance between the receiving planar coil and top surfaces of active amplifier assembly 1560 exceeds the minimum charging distance. In this case, charging cannot occur while the EEG headset is attached to a wearer's head, thus preventing risk of charging-related safety hazards to the wearer.

In another embodiment, an EEG headset stand or clip is used when charging or storing the EEG headset. Such a stand or clip may be used to counteract undesired material creep due to in-use deformation or material creep that may otherwise occur during storage. The stand or clip may be constructed to provide an optimal resting curve for a headband assembly, such as headband assembly 150, and optimal extension for an electrode spring tab, such as electrode spring tab 162.

EEG headset 100 includes an electrode/lead assembly that may comprise external electrode assemblies and/or internal (and predominantly non-visible) leads. Electrode assemblies, examples of which are shown as, but not limited to, electrode assemblies 110, 111, may include one or more user selectable and configurable leads. Each lead may be formed to accept one or more EEG electrodes (e.g., one or more of electrodes 116-118) and/or one or more sensors (not shown). In one example, a user may select a size, shape, and electrode positioning of a lead, from among a plurality provided, such that the one or more electrodes attached to the lead nominally align with desired nominal anatomical locations. Alternatively or additionally, a user may select from among a plurality of pre-configured lead sets, each set containing one or more leads. A selectable lead set may be configured to meet specific electrode anatomical-position requirements, such as those of a medical procedure. Further, custom lead shapes, sizes, and configurations may be fabricated to user specifications. In the present example, electrode assemblies 110, 111 and/or electrodes 116, 117, and 118 may be disposable (single use), reposable (limited number of uses), or non-disposable (use limit not stated).

In an embodiment, electrodes may be attached to rigid, semi-rigid, and/or conformable portions of the EEG headset by way of a connector, an example of which is snap button 364 (FIG. 3).

Figure 2A:
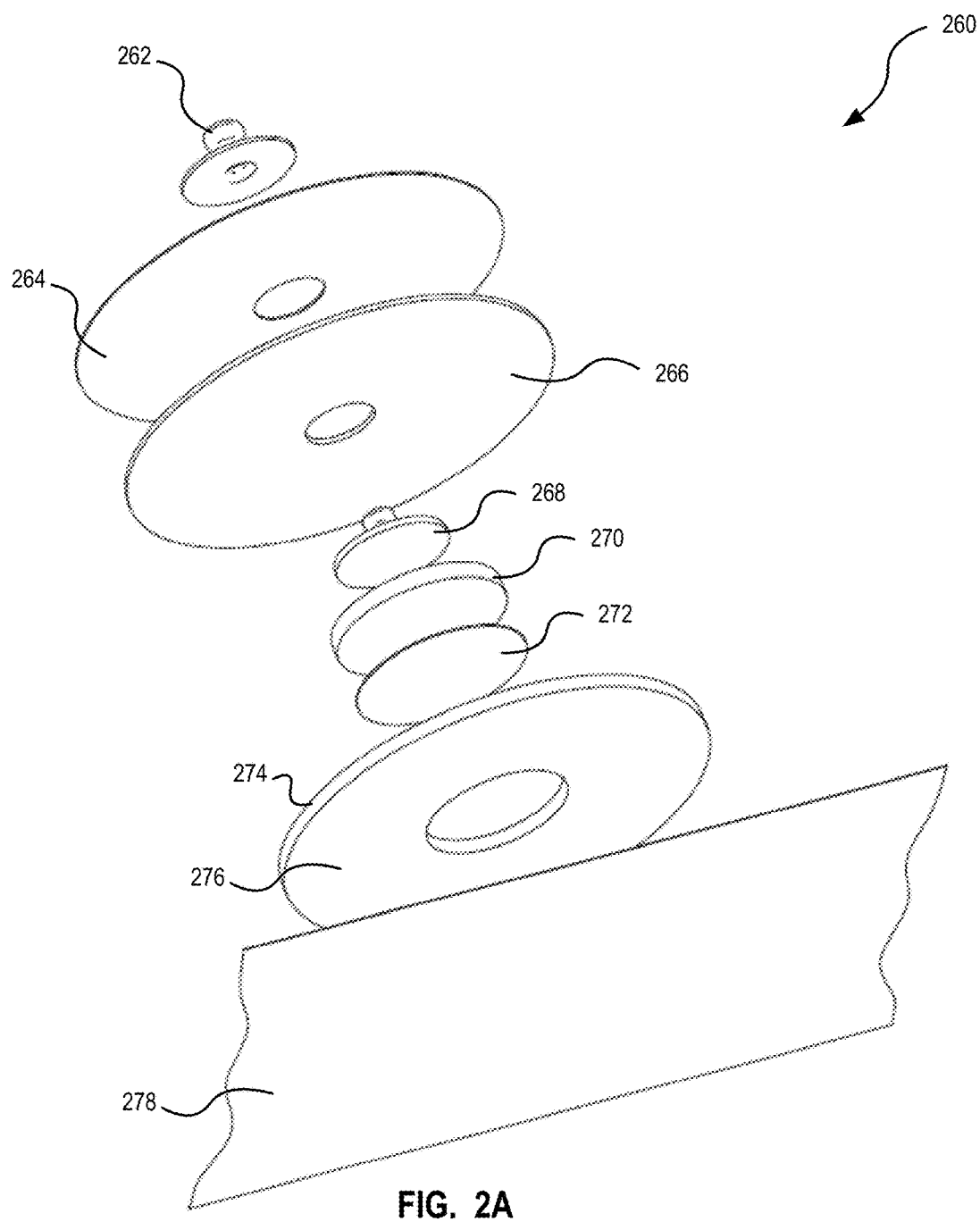
FIG. 2A shows an exploded view of a disposable electrode assembly, in an embodiment.

FIG. 2A shows an exploded view of a disposable electrode 260. Electrode 260 is constructed of a snap plug 262, a label layer 264, a base layer 266, an electrode contact 268, a foam disc 270, a wet gel conductive medium 272, a film or foam layer 274 with an integral biocompatible adhesive 276, and a removable adhesive protection layer 278. Integral adhesive films (not shown) bind adjacent layers and secure foam disc 270. Electrode contact 268 may be formed of silver/silver-chloride (Ag/AgCl) or other low-impedance, low-noise, or low-voltage-offset formulation. Conductive medium 272 may be of any conductive, biologically compatible variety. Where used over the predominantly hair bearing region of the scalp, biocompatible adhesive 276 is formulated to optimize the properties of ease of removal from hair and system stabilization. Where used over relatively hair free regions, biocompatible adhesive 276 may be of a different formulation, such as one that optimizes properties of skin adhesion and ease of removal from skin.

In alternative embodiments, electrodes, such as electrodes 116, 117, and 118, may be of a dry, noncontact (or capacitive), viscous gel, structurally durable hydrogel, adhesive gel, conductive paste, saline or other variety. Electrodes may further be formulated without adhesive for use in pressure bearing electrode locations. Dry, non-contact, and other electrode varieties may include protrusions, depressible or otherwise, to facilitate contact on the skin or through hair. In lieu of or in addition to electrodes 116, 117, 118 or electrode assemblies 110, 111, alternate embodiments of the system may be configured to accept any type of biological or non-biological sensor or emitter, without departing from the scope herein. Examples of such sensors and emitters include, but are not limited to, oxygen saturation, respiration, optical, visible and non-visible light, chemical, resistance, temperature, heart rate, ocular, gaze, nystagmus, and proximity sensors; audio transducers; photic and electrical stimulators; and control signal transmitters.

FIG. 1 shows electrodes 116, and 117, 118 attached to external leads 112, 114, respectively. Electrodes 116, and 117, 118 mechanically and electrically connect to leads 112, 114, respectively, via, for example, a snap button (not shown).

Figure 24:
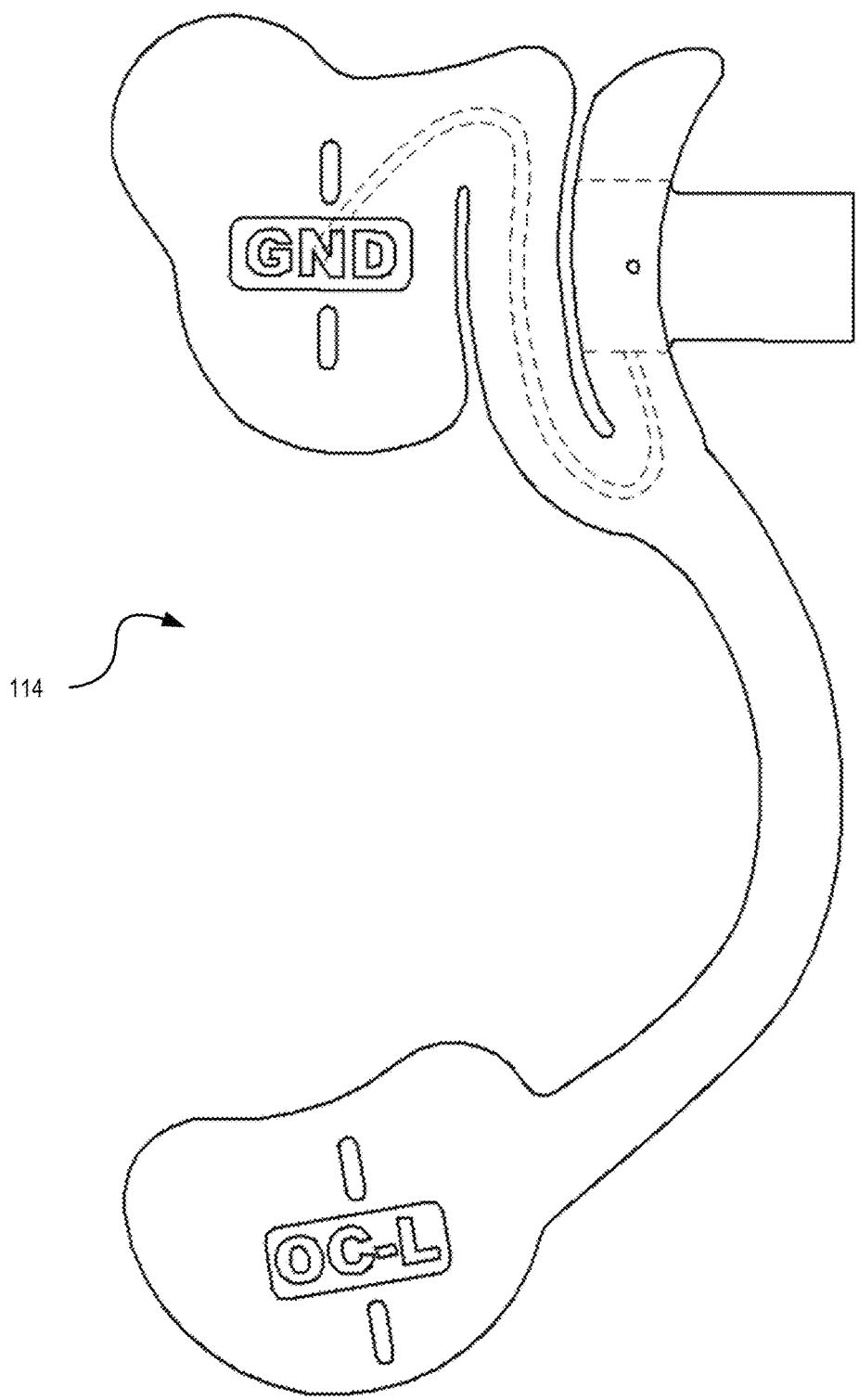
FIG. 24 is a side view of a left lead of an EEG headset, in an embodiment.
Figure 25:
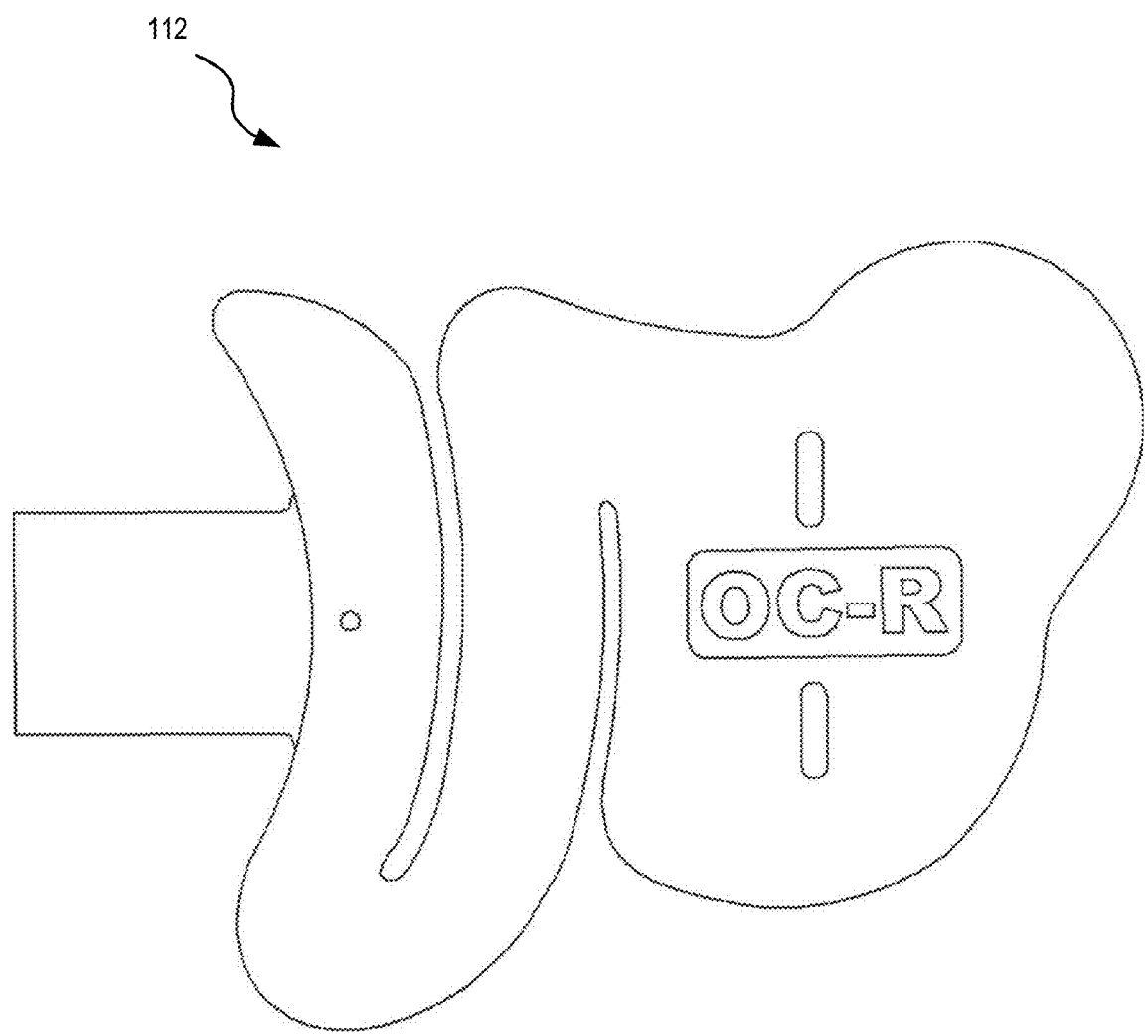
FIG. 25 is a side view of a right lead of an EEG headset, in an embodiment.
Figure 31A:
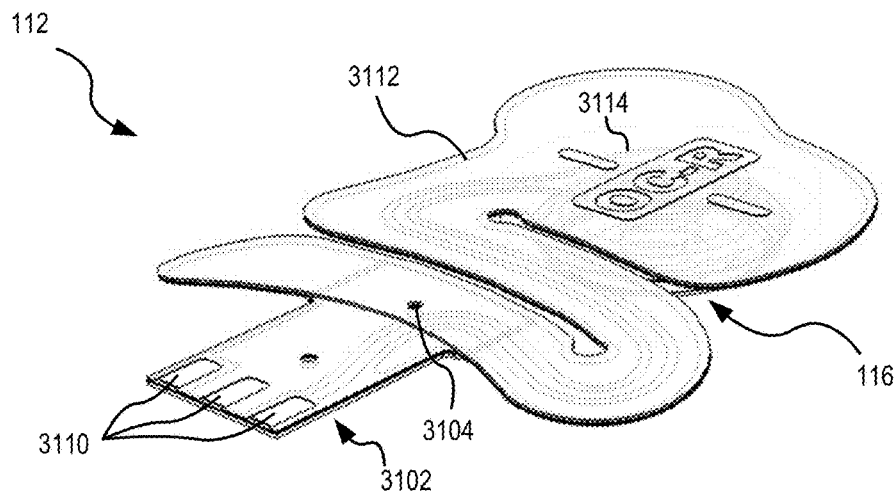
FIG. 31A shows a first perspective view of an exemplary electrode lead with further detail, in an embodiment.
Figure 31B:
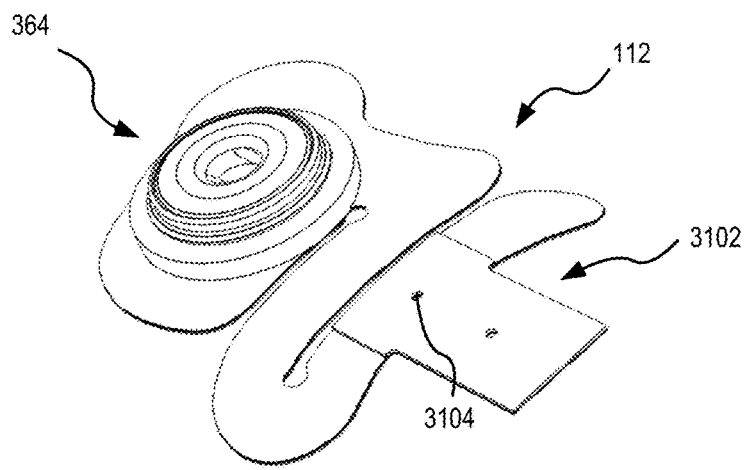
FIG. 31B shows a second perspective view of the electrode lead of FIG. 31A showing the electrode side, in an embodiment.
Figure 31C:
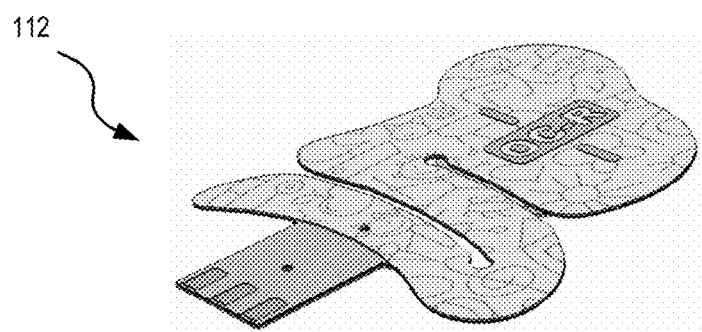
FIG. 31C shows an exemplary ornate embodiment of an electrode lead.

External leads 112, 114 are shown in more detail in FIGS. 25 and 24, respectively. Leads 112, 114 are flat, semi-flexible, and contoured in shape. The positions of electrodes on leads 112, 114, along with the semi-flexible nature of the leads, facilitate alignment of electrodes 116, 117, and 118 at nominal anatomical locations on a wearer. The contours of leads 112, 114, along with the flexible aspect of the leads, facilitate fine-adjustment of electrode locations relative to the nominal anatomical locations. FIGS. 31A-C shows lead 112 in greater detail. For example, FIG. 31A shows tab 3102 supporting lead 112 with conductive contacts 3110 connected to traces 3112 and 3114 for electrical communication with electrode 116 by way of snap button 364. Lead 112 additionally includes a securing aperture 3104 for facilitating mechanical connection to electrode lead plug 132 (see below). FIG. 31B shows the electrode side of lead 112 supporting one embodiment of snap button 364. FIG. 31C shows one ornate embodiment of lead 112.

FIG. 1 shows two example leads with different shapes and electrode capacities: lead 112, configured with a single electrode 116, and lead 114, configured with two electrodes 117, 118. It will be understood that other lead types of similar or alternative design may be formed for attachment to the ear lobes, mastoids, forehead, and other anatomical locations on a wearer.

In an embodiment, leads such as leads 112, 114 may be formed from a plurality of layers, for example, constructed with an upper and lower outer surface label layer, an undersurface microbial inhibiting layer, and an internal thin flexible circuit layer. The internal thin flexible circuit layer may incorporate a plurality of conductive trace-bearing or screen printed layers interspersed with adhesive bound thin polymer films.

Figure 28:
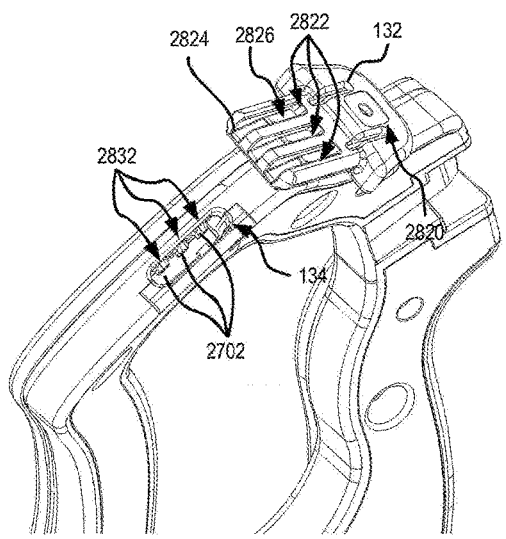
FIG. 28 shows an exemplary electrode lead plug and associated electrode lead jack, in an embodiment.
Figure 32:
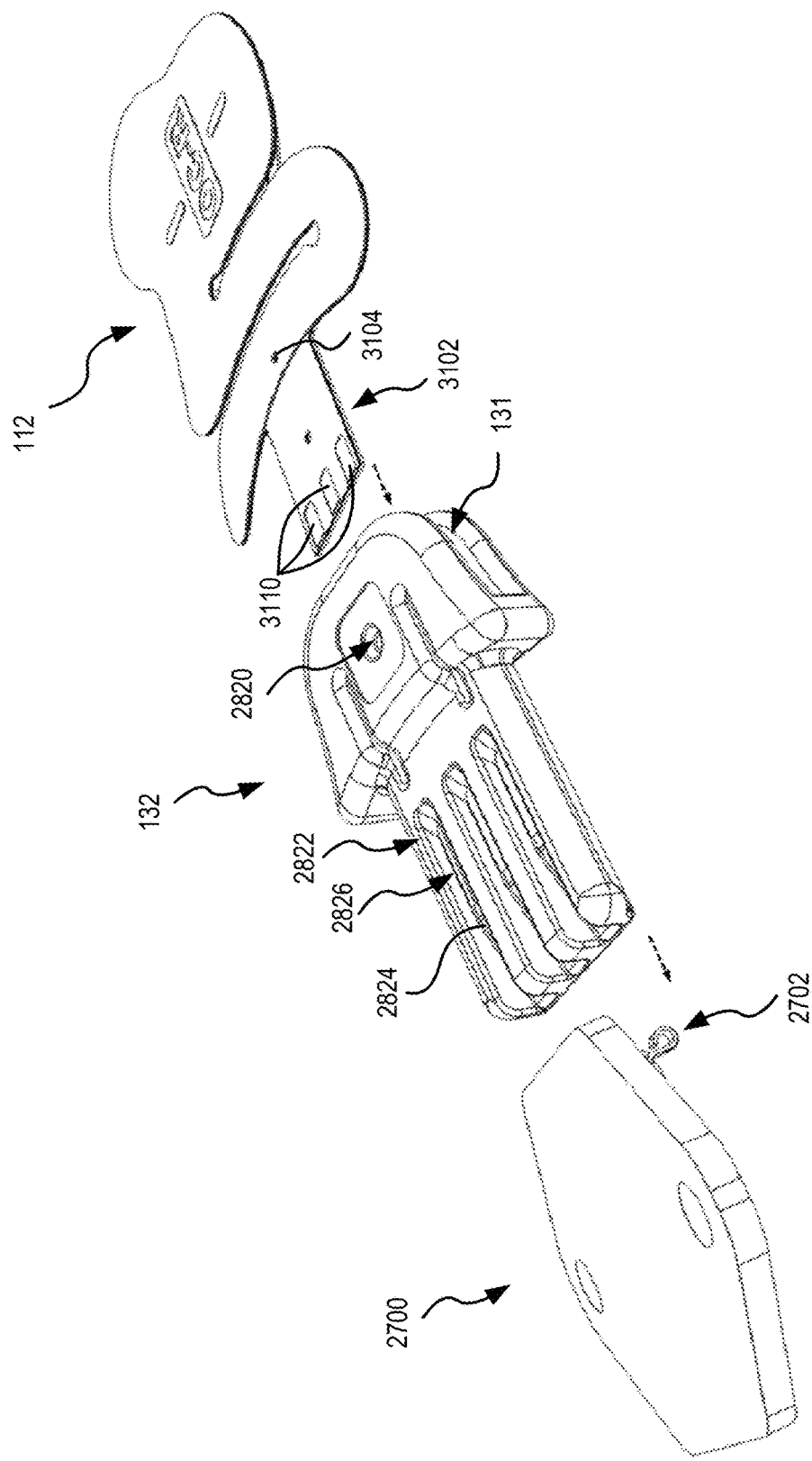
FIG. 32 shows the proper alignment and configuration of exemplary lead, electrode lead plug, and electrode lead PC board, in an embodiment.

In some embodiments, leads may be reinforced with a stiffener layer constructed of, by way of example, a polyimide polymer, glass-fiber-reinforced epoxy, or other suitable material, in the region of system interface. Similar stiffener formulations may optionally be used for reinforcing purposes in the region of electrode attachment to the flexible circuit. Leads 112, 114 connect to electrode lead plug 132, 133, respectively, at lead connecting slot 131 by inserting tab 3102 (see FIGS. 31 and 32 for more detail). Leads 112, 114 are secured to electrode lead plugs 132, 133 by a securing device, for example by a pin, screw, or similar attachment mechanism (not shown) passing through electrode lead plug 132's securing aperture 2820 (FIGS. 28 and 32) and lead 112's securing aperture 3104 (FIGS. 31 and 32). Electrode lead plugs 132, 133 are formed with one or more ramps 2824 for guiding one or more spring contacts 2702 to one or more supplementary slots 2826 (FIGS. 28 and 32). Supplementary slots 2826 expose aligned conductive contacts 3110 (FIG. 31A) of leads 112, 114 for further electrical transport from the electrode, for example electrode 116, to the electrode lead jack PC board, for example PC board 2700. Leads, such as leads 112, 114, may use other types of electrical and mechanical interconnection or may otherwise be constructed with no visible interconnections, without departing from the scope herein.

Figure 27:
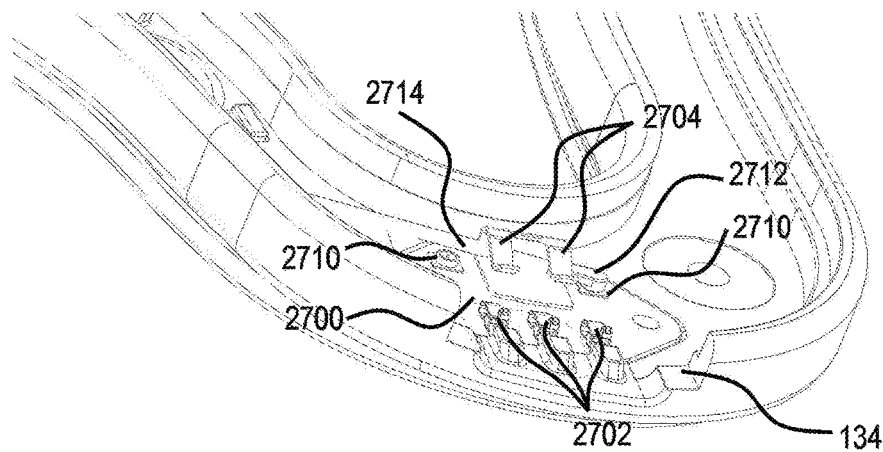
FIG. 27 shows an exemplary electrode lead jack PC board, in an embodiment.
Figure 29:
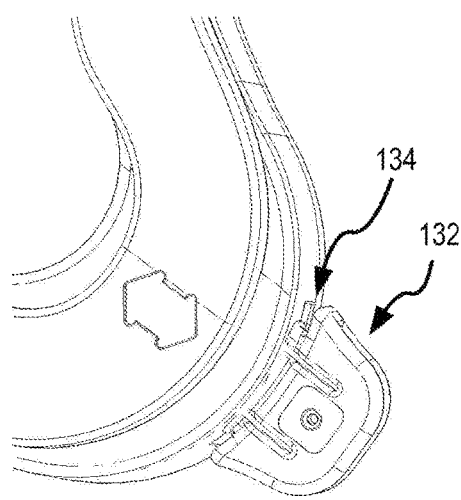
FIG. 29 shows the electrode lead plug and electrode lead jack of FIG. 28 properly mated, in an embodiment.
Figure 30:
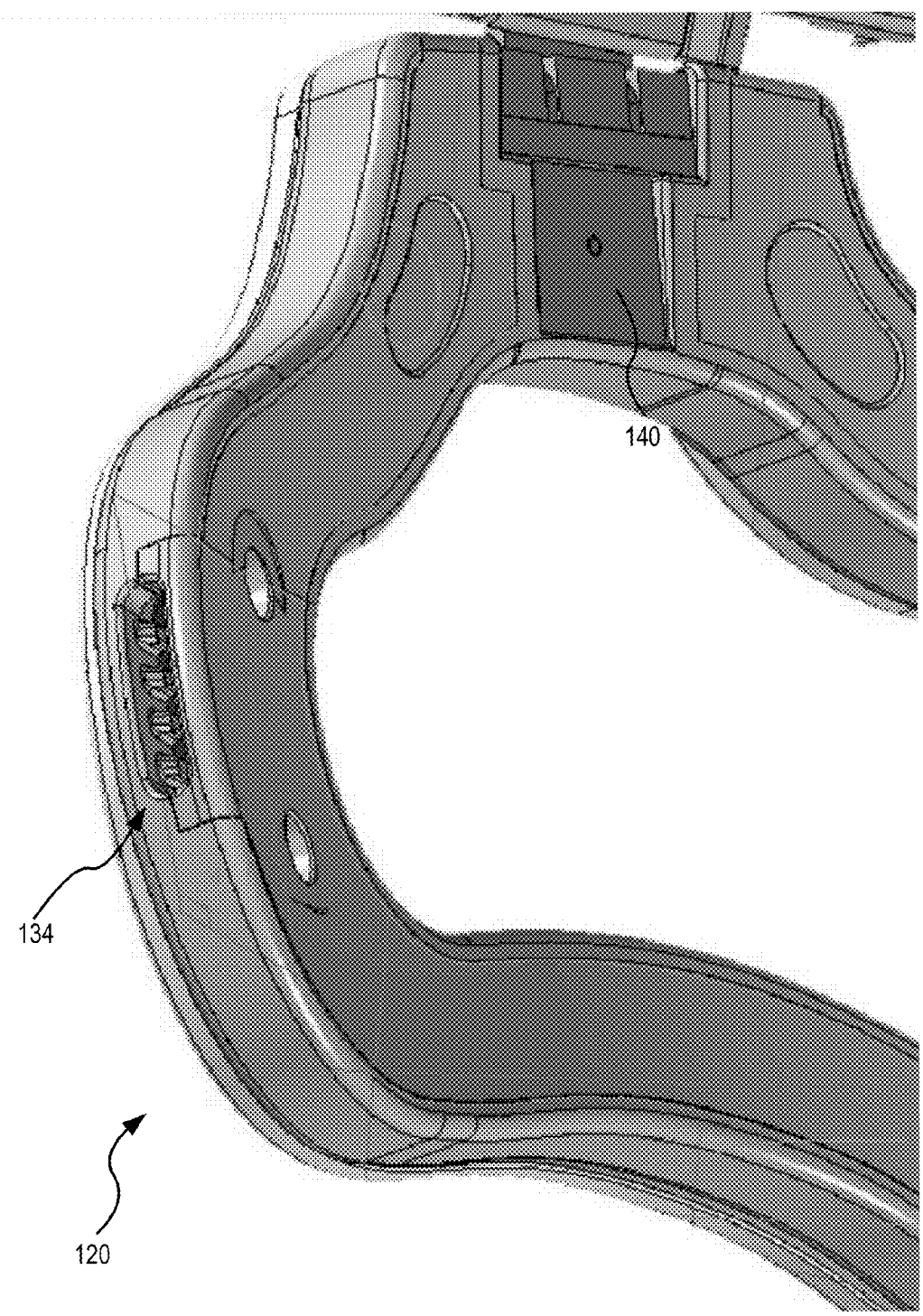
FIG. 30 is a perspective view of an exemplary electrode lead jack, in an embodiment.

Electrode lead jack 134, 135 includes a cavity formed to accept electrode lead plug 132, 133 by insertion. Electrode lead jacks 134, 135 include alignment features 2832 (See FIG. 28 for more detail), which cooperate with alignment features 2822 on electrode lead plug 132 to facilitate alignment between exposed contacts 3110 (FIG. 31A) on lead 112, 114 within supplementary slots 2826 and spring contacts 2702 (see FIG. 27 for more detail) on electrode lead jack PC board 2700 (see FIG. 27 for more detail). For more detail on assembling lead 112 with electrode plug 132 and electrode 132 with electrode lead jack PC board 2700, see FIG. 32. In an embodiment, electrode lead jack PC board 2700 includes a captive detent spring 2704 (FIG. 27), for instance one formed from a spring like metal clip, to assist in the retention of electrode lead plugs 132, 133. Captive detent spring 2704 may be formed in addition to or instead of an integral protrusion on electrode lead plug 132, 133 for mating with a corresponding depression in main lateral support 122. Alternate embodiments may use, for example, a friction fit mating, may rely on mating between spring contacts 2702 and supplementary slots 2826 to secure electrode lead plug 132, 133 in electrode lead jack 134, 135, or may use any other mating system without departing from the scope herein, for mating an electrode lead plug to an electrode lead jack as shown in FIG. 29. The electrode lead jack PC board 2700 may be constructed of 0.8 mm glass-fiber-reinforced epoxy that includes copper traces to provide conduction between spring contacts 2702 and low mating height connector jacks mounted on electrode lead jack PC board 2700.

In an embodiment, electrode lead jacks, examples of which are electrode lead jacks 134, 135, may be formed at any of one or more locations on lateral support assemblies 120, 130, or elsewhere on EEG headset 100. In an additional embodiment, one or more electrode lead jacks may be formed to be any size and shape and/or may formed with a touch-proof-type cavity, such as an industry standard touch-proof jack cavity, for mating with compatible touch-proof plugs 132 configured with leads 112, 114.

In the embodiment shown in FIGS. 1-8, and 27, the low mating height connector jack 2710 is attached to a low profile coaxial connector plug 2712 that may be soldered and/or crimped to a sub-millimeter coaxial internal cable 2714. In an alternative embodiment, the low mating height connector jack 2710 is constructed for mating to a flexible printed circuit connector plug soldered to a flexible circuit (flex circuit) internal lead. Other similar means of connection and internal electrical conduction may be used, without departing from the scope herein.

Figure 16A:
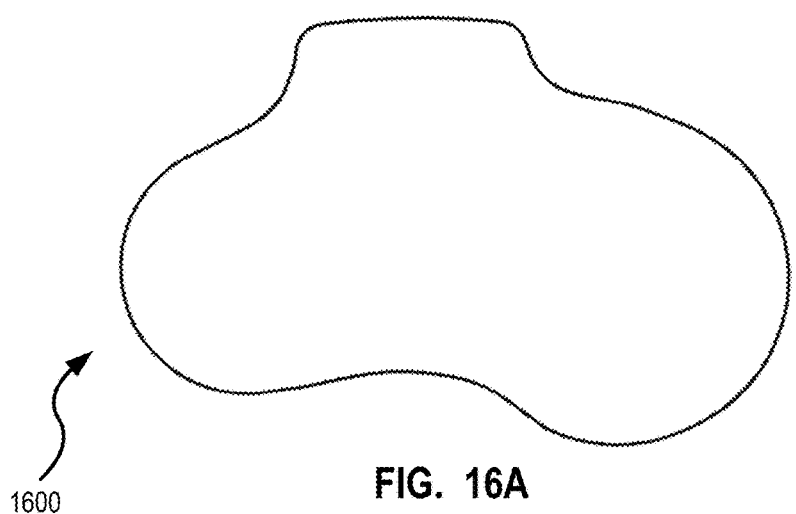
FIG. 16A is a side view of a foam lining for an EEG headset, in an embodiment.
Figure 16B:
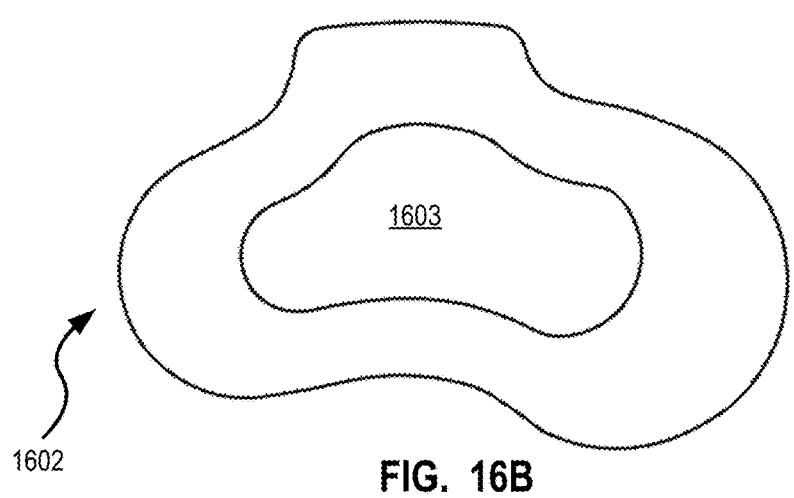
FIG. 16B is a side view of a foam lining for an EEG headset including a cut-out, according to an embodiment.
Figure 16C:
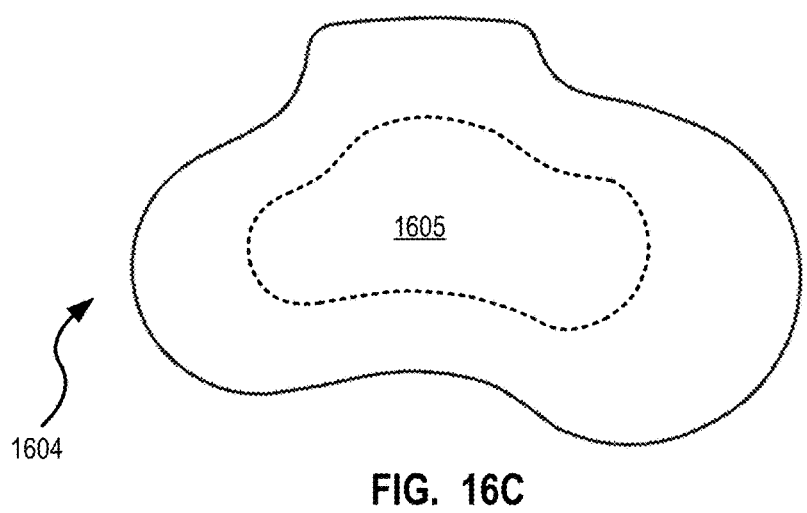
FIG. 16C is a side view of a foam lining for an EEG headset including a recess, according to an embodiment.

Patterns for three exemplary linings 1600-1604 are illustrated in FIGS. 16A-C. In an embodiment, linings 1600-1604 may be detachably connected to lateral support assemblies 120, 130 and may be constructed from a selectable thickness of material and formed by stamping with a steel rule die. Linings 1600-1604 may be disposable or reusable and may further be embossed with a pattern upon manufacture. FIG. 16A shows foam lining 1600 with a substantially smooth, uninterrupted surface. FIG. 16B shows foam lining 1602 that includes a cut out portion 1603. FIG. 16C shows a foam lining 1604 that includes a recessed portion 1605.

An adhesive-backed hook and loop system may be used to secure compressible and/or conformable linings to EEG headset 100 wearer interface surfaces. Alternative methods of attaching linings to EEG headset 100 may be used without departing from the scope herein. Such attachment mechanisms include, but are not limited to, attachment by snap connection, magnetic connection, electromechanical connection, and non-residue-forming adhesive.

Linings, examples of which include but are not limited to linings 1600-1604, may contain or be embedded with one or more electromechanical connectors, one or more electrodes, one or more sensors, one or more emitters, one or more thin wires, and/or one or more flat leads. The electromechanical connectors are formed to participate in the transmission of electrical signals to a processing system. The electromechanical connectors are configured to mate with compatible connectors on the EEG headset. In one example, electrodes are configured with or formed integral to the electromechanical connector. In another example, the electrode is located remote from the electromechanical connector and is electrically connected to the electromechanical connector via one of thin wires or flat leads. In a further example, the lining includes one or more electrode-embedded extensions to form one or more integral, flexible external leads.

Figure 17:
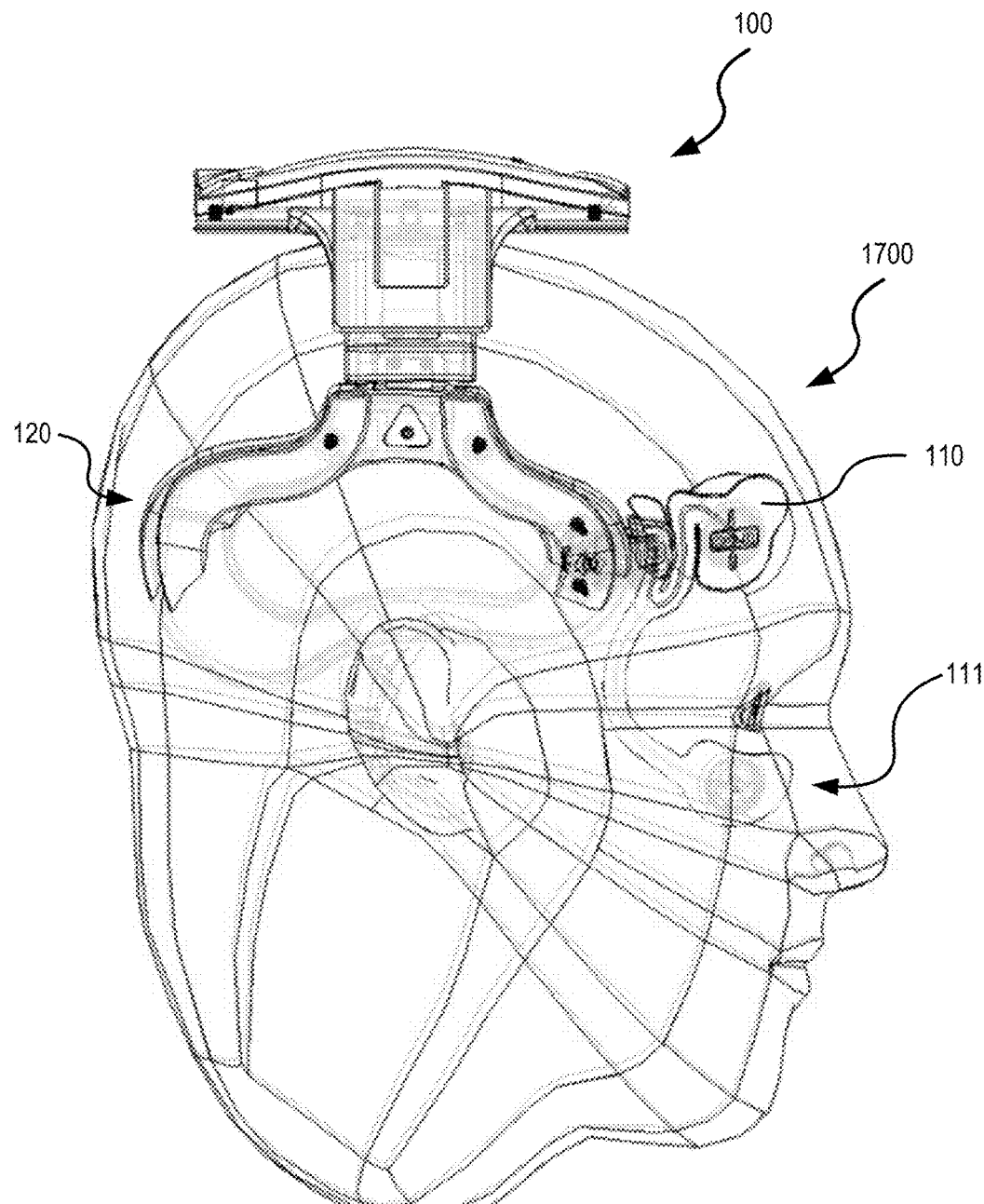
FIG. 17 schematically illustrates an embodiment of the EEG headset of FIG. 1, worn by a person.

FIG. 17 illustrates a wire frame EEG headset 100 secured to a wire frame human head model 1700. For illustration, EEG headset 100 is shown in its relaxed, nominal state rather than its flexed state. FIG. 17 additional shows EEG headset 100 properly arranged on human head model 1700 such that lateral supports 120 and electrode assemblies 110, 111 automatically locate at nominal positions.

Headset and Electrode Location and Placement

Figure 18:
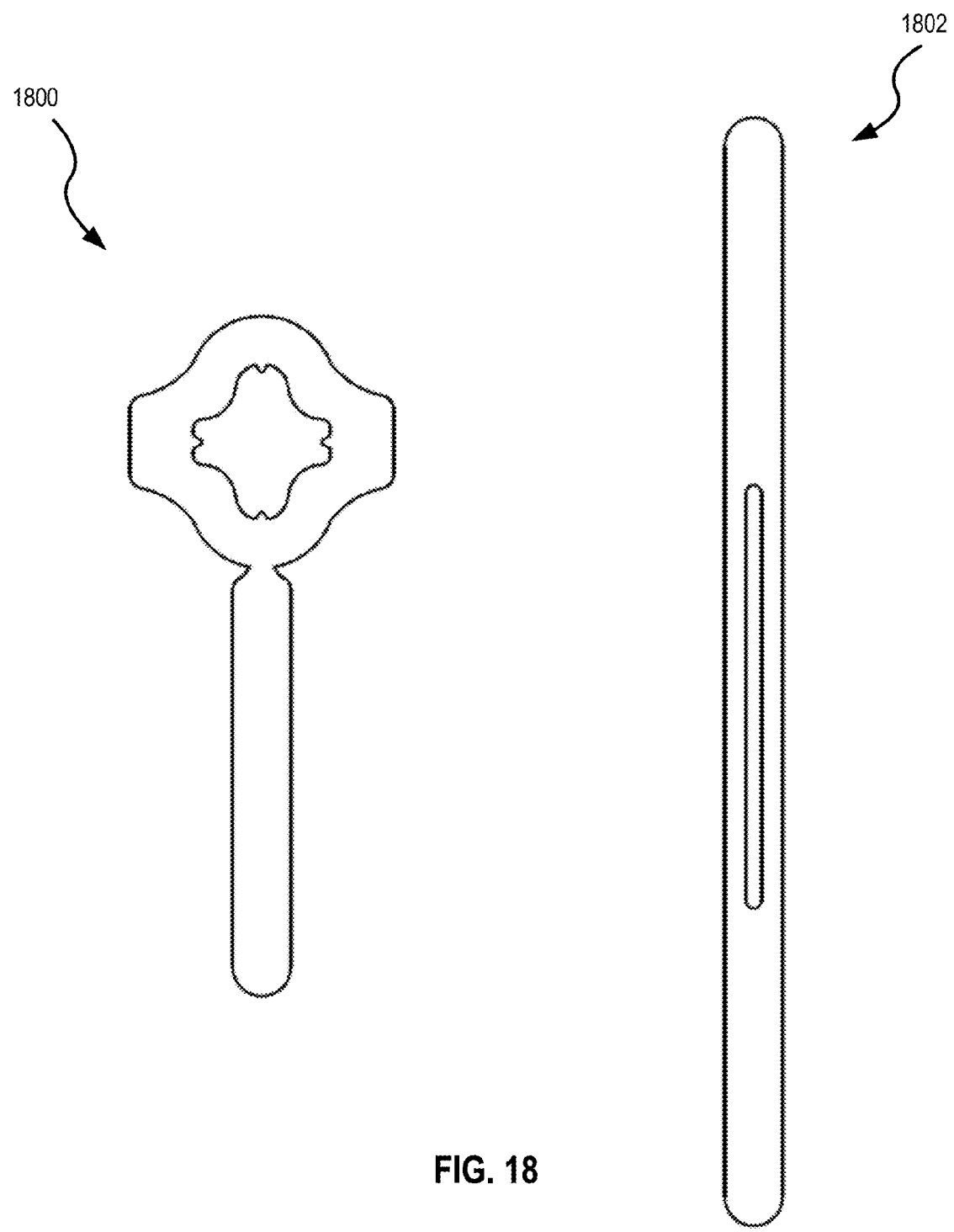
FIG. 18 shows a measurement strip and locator system for properly locating an EEG headset on a person, in an embodiment.
Figure 20:
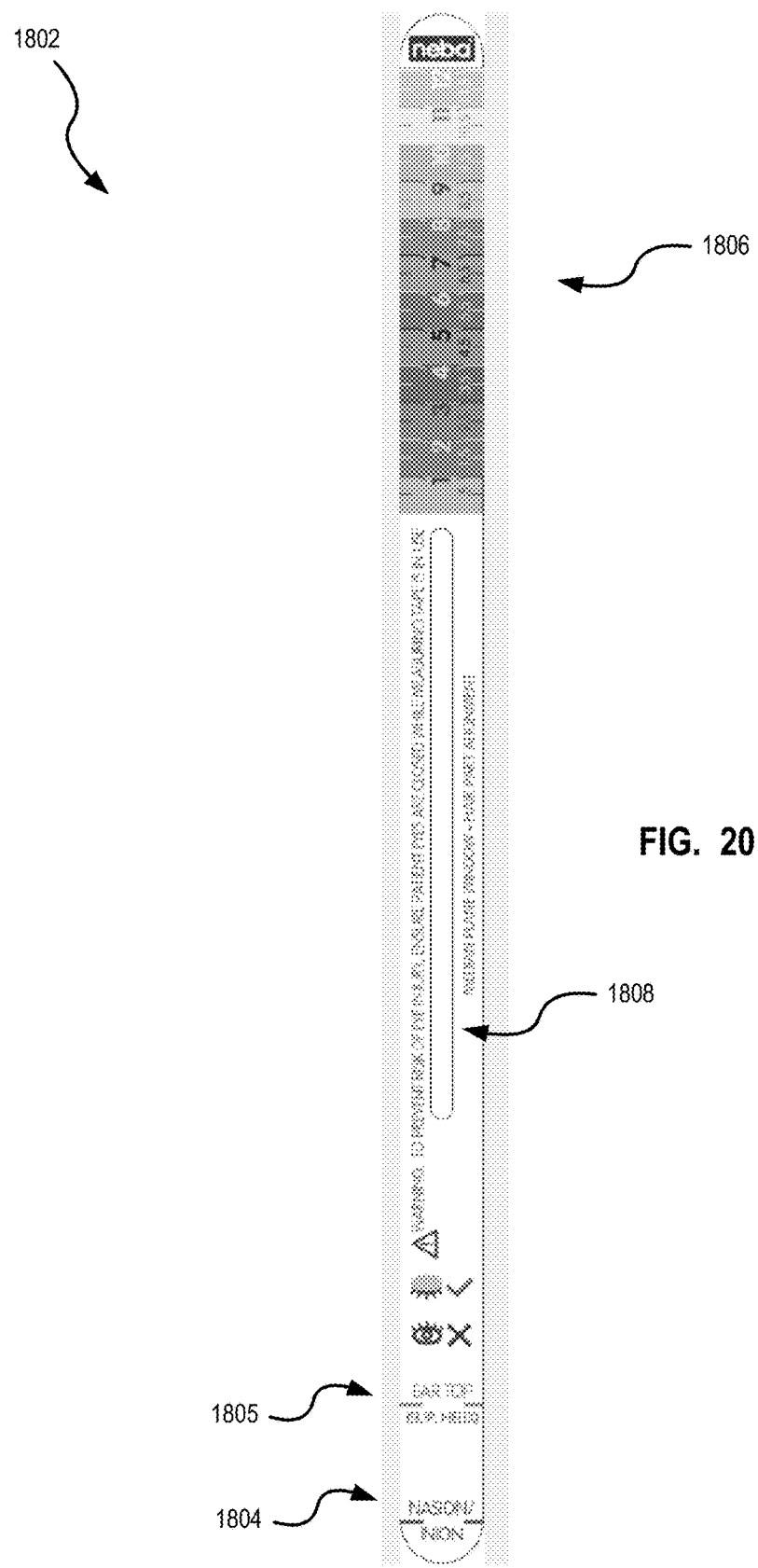
FIG. 20 is a detailed view of the measurement strip of FIG. 18, according to an embodiment.
Figure 21:
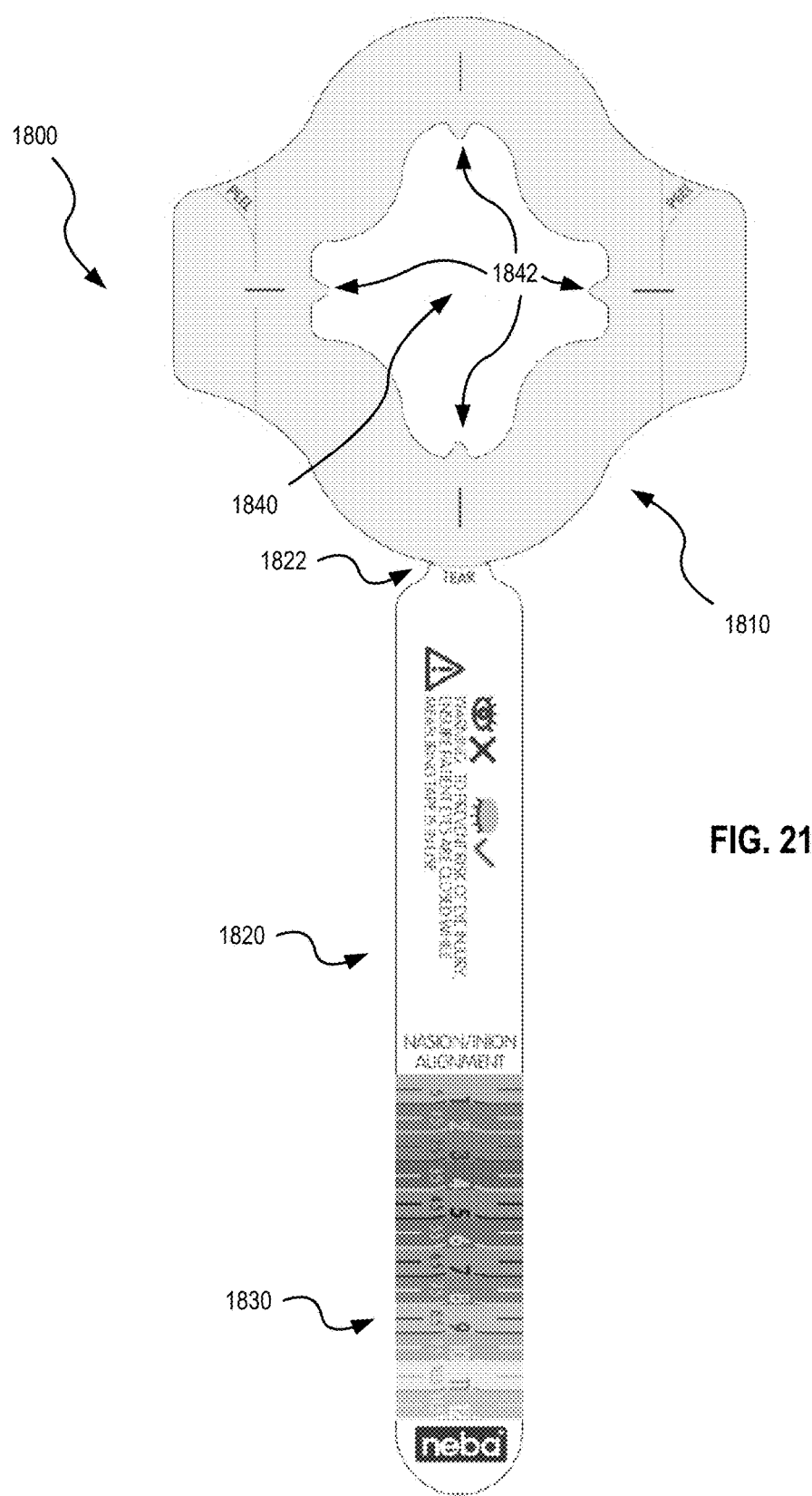
FIG. 21 is a detailed view of the locator system of FIG. 18, according to an embodiment.
Figure 22:
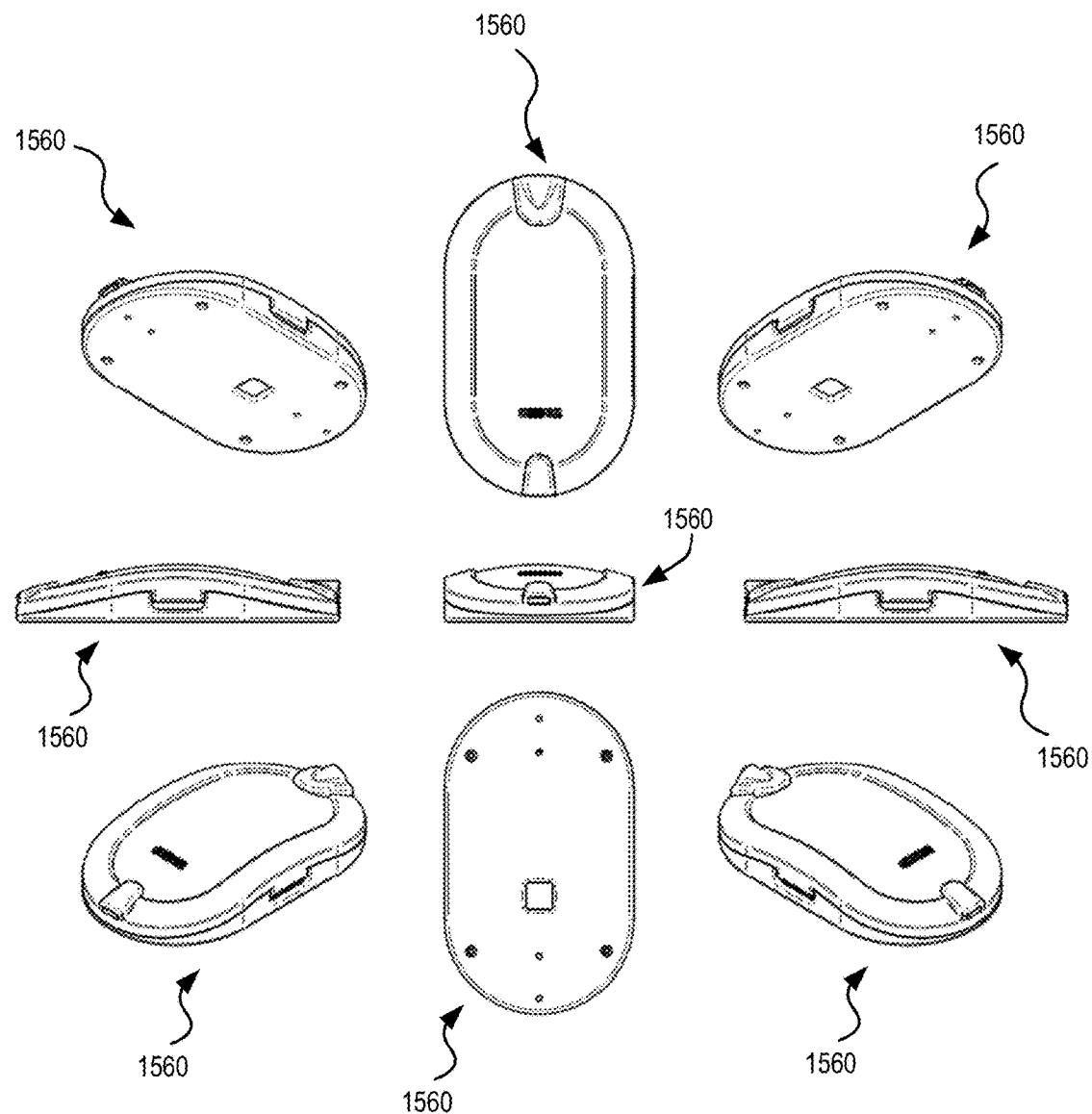
FIG. 22 shows a plurality of views of the amplifier assembly.
Figure 23:
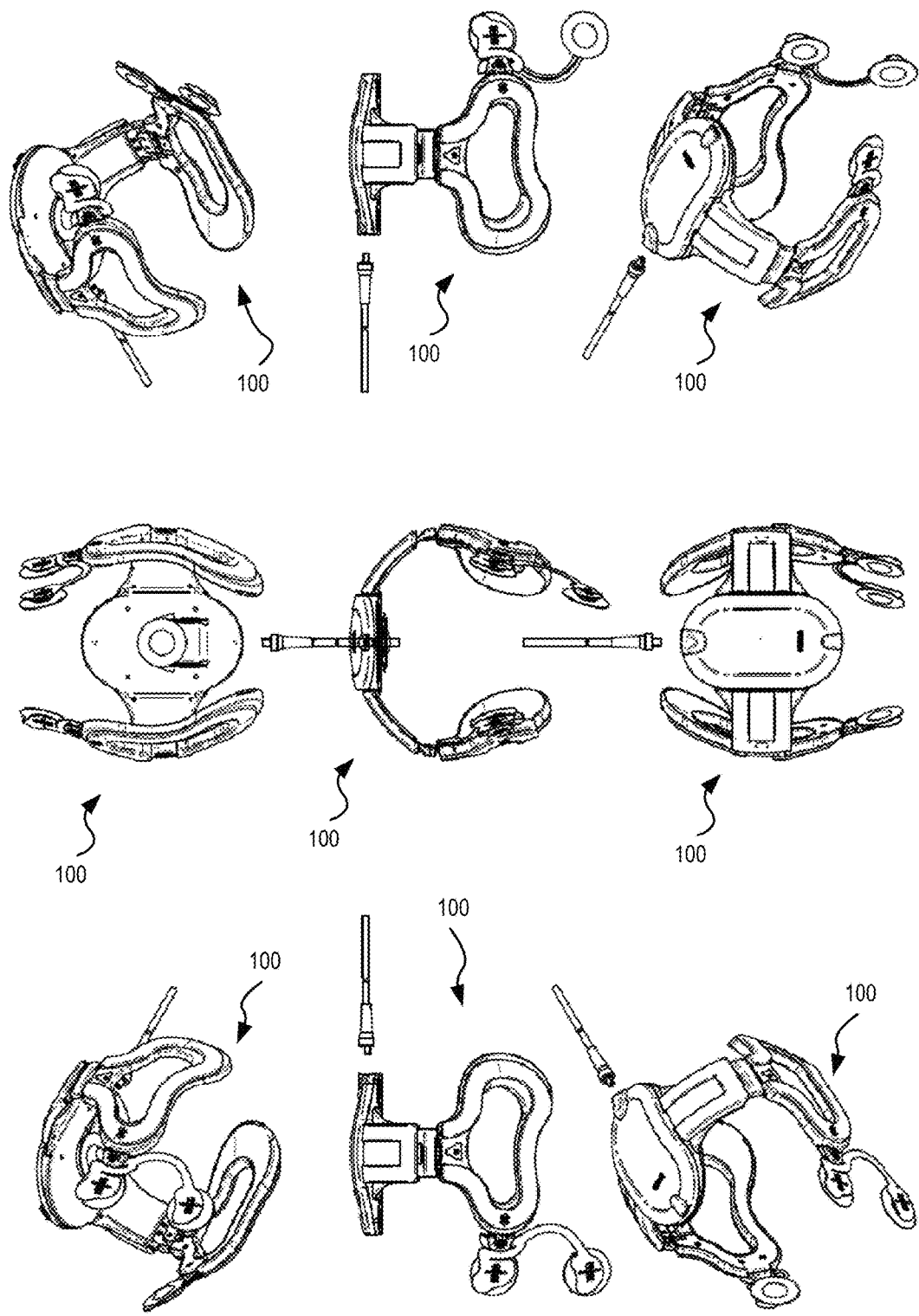
FIG. 23 shows a plurality of views of the EEG headset of FIG. 1, in a wired embodiment.

Though the lower portion 121R, 121L of lateral support assemblies 120, 130 are shaped with an over-the-ear curve for proper placement on the wearer, placement accuracy of EEG headset 100 and individual electrodes 116, 117, and 118 may be additionally or otherwise improved. In one embodiment, headset placement accuracy is facilitated by a headset locator 1800 and locator measurement strip 1802 (see FIGS. 18, 20, and 21). Measurement strip 1802 and headset locator 1800 may be constructed of a thin and flexible coated paper, cloth, and/or synthetic material. Measurement strip 1802 includes on one end a sagittal plane measurement start marker 1804 and on another end a numerical scale 1806. Scale 1806 extends only as much as needed to accommodate head surface anterior to posterior (for instance, nasion to inion), or vice versa, length measurement for the system supported head sizes. Measurement strip 1802 may additionally include a coronal plane start marker 1805 for head surface lateral to contralateral (for instance, left ear superior helix to right ear superior helix) measurement. In an embodiment, the lateral to contralateral measurement may serve to set EEG headset 100 adjustment bands 252R, 252L to the correct head size for fitting on a wearer. Adjustment bands 252R, 252L include, in the present embodiment, a numerical scale whose values are derived directly or from scalar multiples of scale 1806 of measurement strip 1802. In an embodiment, sagittal plane start marker 1804 may be displaced on measurement strip 1802 relative to coronal plane start marker 1805. This displacement serves cases where it is desirable to use the same scale 1806 for both sagittal and coronal measurements but where the supported measurement ranges differ. Scale 1806 may be color coded to facilitate adjustment of a correspondingly color coded scale on adjustment bands 252R, 252L and/or a scale 1830 on headset locator 1800 (described below). Measurement strip 1802 further includes a median plane window 1808 to facilitate location of a hair parting line.

Headset locator 1800 is shaped to facilitate alignment of EEG headset 100 on a wearer's head. Headset locator 1800, in one embodiment, is formed with a placement area 1810, locator scale tab 1820, and locator scale 1830. Locator scale 1830, in one embodiment, is half the scale of measurement strip 1802 scale 1806. By using this scale ratio, a center point 1840 of headset locator 1800 may be positioned at the center of the wearer's head by using only one head reference point (for instance, the nasion or inion). Once centered, placement area 1810 may be secured to the wearer's head by hair compatible adhesive or other method and detached from locator scale tab 1820 by use of a perforation along an attachment line 1822. EEG headset 100 may then be located on the head of the wearer by aligning amplifier platform 156 or amplifier assembly 160 with secured placement area 1810. To improve skin contact, hair parting lines may be selected to intersect with desired electrode locations (for instance, a location centered at snap button 364) and may differ from natural hair parting lines. EEG headset 100 maintains an operator selected hair parting line utilizing pressure generated by, for example, one or more of the weight of EEG headset 100, spring action of electrode spring tab 362, and EEG headset 100 retaining pressure generated by headband assembly 150, lateral support assemblies 120, 130, and hinges 140.

In an embodiment, an upper surface of headset locator 1800 may include a double-sided adhesive to facilitate securing EEG headset 100 to the wearer.

Measurement strip 1802 and headset locator 1800 may further be constructed of a disposable low-cost paper or other suitable material. Disposability reduces risk of microbial transmission relative to non-disposable measurement tapes. Where measurement strip 1802 and headset locator 1800 are non-disposable, they may incorporate an antimicrobial material, treatment, or texture.

Although shown as separate parts, it will be appreciated that measurement strip 1802 and headset locator 1800 may be combined as a single construction, for example with two optionally removable strip extensions. In another embodiment, electrode position measurement strips may be radially located at discrete angles relative to each other, corresponding to placement angles of desired electrode locations on the scalp. In some embodiments, measurement strip 1802, headset locator 1800, and combined constructions thereof, may be formed of a clear material, demarcated or otherwise.

In an alternative embodiment, a headset locator, such as headset locator 1800, is not used for accurate headset placement. Instead, a thin flexible measurement strip with a measurement scale along its length is temporarily attached to the center of amplifier assembly 160 and is configured to rotate about the attachment point. Rotation about the attachment point facilitates locating the EEG headset between anatomical points on the head, for example, between the nasion and inion anatomical locations. The rotatable measurement strip also facilitates identifying electrode positions that reside at relative angles from a nominal measurement strip angle. Attachment of the measurement strip may be accomplished by pressing a flexible tabbed cutout on the measurement strip over a protrusion formed on amplifier assembly 160. An alternate method of attachment is by mating magnets or by mating ferrous material and magnets. Other suitable attachment devices and methods may be used that permit the measurement strip to rotate, without departing from the scope herein. In some embodiments, the measurement strip is rotated to align, balance, or measure anatomical reference points and electrode locations on the head. In some embodiments, angles may be demarcated on amplifier assembly 160 to accurately align the measurement strip to a desired angular position. In one embodiment, a slidable tab may be located on measurement strip 1802 to dynamically demarcate a relative or absolute anatomical position along the measurement strip length. The tab may be constructed to retain its position during measurement strip rotation so as to aid the locating of anatomical reference points and relative electrode positions on the head.

FIG. 26 details one exemplary embodiment of a method 2600 for quickly and accurately fitting an EEG headset to a wearer's head via a single head reference point using headset locator 1800 and measurement strip 1802.

In step 2602, method 2600 aligns a sagittal plane measurement start marker located at the proximal end of a measurement strip with the wearer's nasion. In one example, a practitioner, who is fitting EEG headset 100 to a user wearer, aligns sagittal plane measurement start marker 1804 of measurement strip 1802 with the wearer's nasion.

In step 2604, method 2600 locates where the wearer's inion meets a measurement scale at the distal end of the measurement strip. In one example, the practitioner runs measurement strip 1802 from the nasion to the inion and aligns a numerical value on the measurement strip with the wearer's inion.

In step 2606 of method 2600, a measurement is read from the measurement/numerical scale corresponding to the location of the inion on the measurement/numerical scale. In one example, the practitioner reads a value from the measurement/numerical scale 1806 at the location where the inion meets measurement/numerical scale 1806.

In step 2608, method 2600 identifies on a locator scale at the proximal end of a headset locator a locator measurement corresponding to the value read from measurement/numerical scale 1806. In one example, the practitioner identifies on locator scale 1830 of headset locator 1800 a locator measurement corresponding to the measurement read from measurement strip 1802.

In step 2610 of method 2600, the practitioner aligns the locator measurement with the wearer's nasion. In one example the practitioner aligns the locator measurement on locator scale 1830 with the wearer's nasion.

In step 2612 of method 2600, the practitioner identifies a center point of the wearer's head at the distal end of the headset locator for accurately fitting the EEG headset to the wearer's head. In one example, the practitioner, while maintaining the locator scale on the wearer's nasion, identifies the center point on the wearer's head by running headset locator 1800 from the nasion to its farthest extent on the wearer's head, along the sagittal plane. When the headset locator reaches its farthest extent along the sagittal plane, the center of the head is located.

Optional steps, not discussed above, may include parting a wearer's hair along a sagittal place (also referred to as the median plane or centerline, herein) of the wearer's head and aligning an alignment feature of the measurement strip, for example, the median plane window 1808, with the centerline part.

In addition, method 2600 may include an optional step of aligning, and optionally adhering, headband 159 of EEG headset 100 to placement area 1810. It will be appreciated the size and shape of placement area 1810 is formed to match the size and shape of headband 159, such that matching headband 159 with placement area 1810 facilitates a proper alignment of EEG headset 100. EEG headset 100 may be configured with placement area 1810 either after placement area 1810 is located on the wearer's head or prior. Alignment features 1842 associated with placement area facilitate alignment of placement area with the aspects of the wearer's head, for example, the median line associated with the hair part formed on the wearer's head. Additionally, alignment features 1842 cooperate to identify center point 1840.

In an additional embodiment, an electrode protector may be detachably attached to electrode spring tab 362 (FIG. 3) as a method of preventing biocompatible adhesive 276 and wet gel conductive medium 272 (FIG. 2A) from contacting hair and skin during placement of EEG headset 100. The electrode protector may be detached, for example by slide action, once EEG headset 100 is positioned at a desired location. This mechanism prevents undesired adhesion by biocompatible adhesive 276 and smearing by wet gel conductive medium 272 during EEG headset 100 placement. In an alternative embodiment, an electrode protector is formed by a flat, folded protection film that may be pulled to expose an electrode adhesive and/or gel.

In an embodiment, electrodes, sensors, and sets thereof may be configured and/or optimized for use in or in association with one or more clinical conditions, including, but not limited to, use as a diagnostic or assessment aid for Attention Deficit Hyperactivity Disorder (ADHD), depression, dementia, and/or traumatic brain injury. Configured and optimized electrodes, sensors, and sets thereof may further be detachably attached to the EEG headset such that a single EEG headset may be configured for a plurality of diagnostic and assessment purposes. Alternatively, a unique EEG headset may be designed and fabricated for each diagnostic or assessment criterion.

In some embodiments, including the embodiment of EEG headset 100, the EEG headset is aesthetically designed to convey a sense of "professional", "medical", and "fun" as opposed to "scary", "science fiction", "cheap", and "homemade". Further, the EEG headset is designed, in some embodiments, to evoke a perception that is suggestive, in scaled ornamental characteristics, of the non-anxiety provoking aspects of MRIs, ultrasounds, and similar diagnostic medical devices. In one embodiment, visible parts of the EEG headset, including rigid and flexible components, applied labels, and cover films, are ornamented with patterns, images, and color schemes. In an additional embodiment, the features and ornamental characteristics of visible parts are specifically designed to reduce wearer anxiety (a state of mind that may undesirably impact the EEG in some situations), and/or increase acceptability and interest of a wearer or operator, or demographic thereof.

The EEG headset, in a further embodiment, is formed to accept colored, patterned, and/or illustrated leads, electrodes, linings, low-tack decals, and other components, one example of which is shown as an ornate embodiment of lead 112, FIG. 31C. A user may select one or more ornamentation characteristics for detachable attachment so as to selectively appeal to a wearer or operator, or demographic thereof. These detachable components may, for example, be designed to appeal to the gender, age, and interests of a wearer. Such interests may include, but are not limited to, hobbies, sports, cartoons, animals, designer patterns, and famous or fictional people, places, or objects. In some embodiments, one or more ocular area leads or electrodes may be ornamented in shape and graphic surface to resemble anti-glare decals (or grease paint) popularized in or associated with American football and other sports. In a related embodiment, a display screen (for instance, an EEG monitor display screen) may display images and produce sounds from among a selectable set of images and sounds that appeal to the gender, age, and interests of a viewer and listener. The selectable images and sounds may optionally coordinate with the selectable ornamental components of the EEG headset.

In some embodiments, individual electrodes and leads are not visibly prominent in the design, are flat and anatomically conforming, and/or are laminated with child appealing graphics.

In an embodiment, the amplifier, headband, and/or lateral support assemblies have smooth surfaces without raised lips or edges. In some embodiments, the amplifier assembly is a low profile design combined with top (and optionally, bottom) surface curvature in both coronal and sagittal directions. In some embodiments, the design of the lateral support assemblies are distinguished by their unique profiles, ergonomic contours, and layering.

In an embodiment, triangle-like or sinusoid-like folds on the electrode lead are made orthogonal to the primary plane of the electrode lead to further improve the compression and extension range of the lead.

In some embodiments, shaped electrodes may be used such that, when affixed to a wearer's head or body, the electrode shape limits the possibility of anatomical interference and limits contact with skin regions prone to movement or irritation. Examples of shaped electrode leads are a butterfly or a crescent shaped electrode. In the example of a crescent shaped electrode, it may be beneficially used for ocular region attachment to reduce the probability of ocular and facial discomfort.

One or more internal and external electrode leads may be shielded. Leads that are shielded may cooperate with a signal generator to send a signal into a first end of the shield. The signal may be, for example, proportional to a combination of input signals. In an embodiment, a second end of the shield is not connected.

Electrodes, electrode leads, or extending elements of EEG headset 100 may be of an active design; that is, powered at or in close proximity to an electrode, sensor, and/or emitter location.

Figure 33:
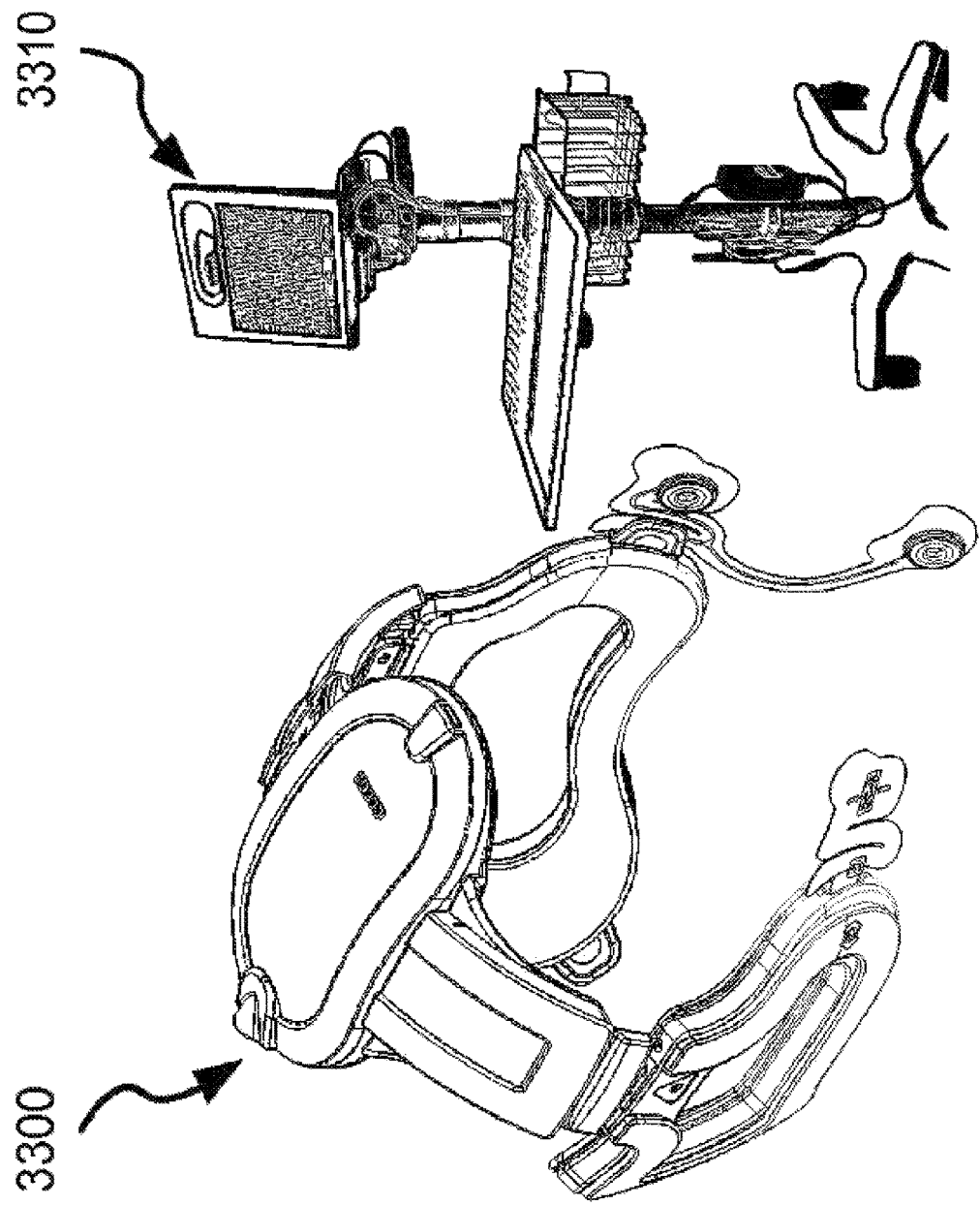
FIG. 33 shows an exemplary EEG headset system, in an embodiment.

FIG. 33 shows one exemplary EEG system 3300. System 3300 includes EEG headset 100 in communication with EEG processing system 3310. EEG processing system 3310 receives and processes data sent from EEG headset 100 for display and analysis. EEG processing system 3310 may be located proximate to EEG headset 100 or may be a remote system. In addition, processing of data collected by EEG headset 100 may occur in real time as data is collected or may be processed at a later time. EEG processing system 3310 may, for example, be typical of systems known in the art.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. An EEG headset system, comprising:
an amplifier assembly;
a headband assembly configured to fit over a wearer's head and formed of a right headband arm, a left headband arm and an amplifier platform configured to support the amplifier assembly;
right and left lateral support assemblies configured to sit proximate the wearer's right and left temporal fossae respectively and each of the lateral support assemblies are formed with an anatomically conforming curvature to cover most of the temporal fossa having a first curve that is substantially in the anterior-posterior direction and a second curve that is substantially in the superior-inferior direction and to leave the wearer's ears unobstructed;
a left hinge assembly connecting the left lateral support assembly to the left headband arm, the left hinge assembly including a spring configured to automatically adjust an angle of the left lateral support assembly by biasing the left lateral support assembly inward to exert lateral support on the wearer's left temporal fossa;
a right hinge assembly connecting the right lateral support to the right headband arm, the right hinge assembly including a spring configured to automatically adjust an angle of the right lateral support assembly by biasing the right lateral support assembly inward to exert lateral support on the wearer's right temporal fossa; and
an EEG electrode disposed within one of the right and left lateral support assemblies;
wherein the EEG electrode is in electrical communication with the amplifier assembly via electrical connection disposed within the headband assembly.

2. The system of claim 1, wherein the EEG electrode is connected to the headband assembly with a flexible lead.

3. The system of claim 2, wherein the flexible lead comprises one of either an active or a driven shield lead.

4. The system of claim 1, wherein the EEG electrode is configured to monitor a condition of the wearer based on one or more characteristics of the wearer's brain function.

5. The system of claim 1 further comprising a releasable electromechanical connection between the EEG electrode and the headband assembly.

6. The system of claim 5, wherein the EEG electrode is selected from the group consisting of a disposable electrode, a reposable electrode, a non-disposable electrode, an electrode including a conductive medium, an electrode including an adhesive, and an electrode including an adhesive and a removable adhesive protection layer, and a releasable electrode.

7. The system of claim 5, further comprising a plurality of EEG electrodes and releasable electromechanical connections between the plurality of EEG electrodes and the headband assembly.

8. The system of claim 5, further comprising a plurality of EEG electrodes and releasable electromechanical connections between the plurality of EEG electrodes and one of the lateral support assemblies.

9. The system of claim 1, wherein the headband assembly is shaped to be substantially self-locating on the wearer's head.

10. The system of claim 1, further comprising a headset locator for accurately aligning and locating elements of the system with anatomical landmarks of the wearer's head.

11. The system of claim 1 further comprising multiple EEG electrodes.

12. The system of claim 11, further comprising an interface for communicating signals from the multiple EEG electrodes to an external signal acquisition and analysis system.

13. The system of claim 11, wherein the left and right springs are configured with the left and right lateral support assemblies to isolate the multiple EEG electrodes from motion occurring at electrode-bearing regions.

14. The system of claim 1, further comprising a microprocessor for receiving and analyzing signals from the EEG electrode.

15. The system of claim 1, further comprising a liner for lining at least a portion of the headband assembly, the liner selected from the group of a conformable material lining, an elastic band, an anti-microbial lining, a textured lining, an expanding support structure, an adhesive-lined film, and a sensor-embedded lining.

16. The system of claim 1, the headband assembly being length-adjustable.

17. The system of claim 1, wherein the left and right springs are selected from the group consisting of a spring hinge, a springy member, a curved spring wire, a curved spring band, a curved spring plate, and an integrated springy member.

18. The system of claim 1, further comprising a first isolation feature attached to the EEG electrode and to either the left or the right lateral support assembly which has the electrical connection disposed within it, for isolating the EEG electrode from mechanical movement.

19. The system of claim 18, further comprising a second EEG electrode and a second isolation feature attached to the second EEG electrode.

20. The system of claim 19, wherein the isolation features comprise flexible leads with at least 4 degrees of freedom.

21. The system of claim 19, wherein the first and second isolation features are formed and configured to reduce triboelectric noise.

22. The system of claim 1, further comprising an electrode spring tab attached to the EEG electrode and configured to maintain electrode pressured contact with skin of the wearer.

23. The system of claim 1, wherein the amplifier assembly is configured with a lower spring tab supporting an EEG electrode for pressured contact with the wearer's skin; and wherein the headband assembly is configured and arranged to translate outward pressure on the right and left lateral support assemblies through the right headband arm and the left headband arm to cause a downward pressure on the lower spring tab and its associated EEG electrode.

24. The system of claim 1, wherein the EEG electrode is selected from the group consisting of a dry electrode, a noncontact electrode, a capacitive electrode, a viscous gel electrode, a structurally durable hydrogel electrode, a conductive paste electrode, a saline electrode, and an adhesive gel electrode.

25. The system of claim 1, wherein the first and second curves vary in curvature.

26. The system of claim 1, wherein the EEG electrode is selected from the group consisting of an active electrode, a shielded electrode, and an actively shielded electrode.

27. The system of claim 1, wherein the EEG electrode is connected to one of the lateral support assemblies with a flexible lead.

28. The system of claim 1 further comprising a releasable electromechanical connection between the EEG electrode and one of the lateral support assemblies.

* * * * *